United States Patent
Mitani et al.

(10) Patent No.: US 9,007,449 B2
(45) Date of Patent: Apr. 14, 2015

(54) ELECTRONIC ENDOSCOPE

(75) Inventors: Takahiko Mitani, Hachioji (JP);
Kazuhiro Kumei, Tachikawa (JP);
Kazuyoshi Akiba, Hachioji (JP); Seiji Sakai, Chofu (JP); Hironobu Ichimura, Akishima (JP); Masahiro Kawauchi, Akiruno (JP)

(73) Assignees: Olympus Medical Systems Corp., Tokyo (JP); Olympus Corporation, Tokyo (JP)

( * ) Notice: Subject to any disclaimer, the term of this patent is extended or adjusted under 35 U.S.C. 154(b) by 1579 days.

(21) Appl. No.: 11/649,974

(22) Filed: Jan. 5, 2007

(65) Prior Publication Data
US 2007/0118019 A1    May 24, 2007

Related U.S. Application Data

(63) Continuation of application No. PCT/JP2005/012417, filed on Jul. 5, 2005.

(30) Foreign Application Priority Data

Jul. 5, 2004   (JP) ................. 2004-198527
Mar. 7, 2005   (JP) ................. 2005-062926

(51) Int. Cl.
*A62B 1/04*      (2006.01)
*A61B 1/05*      (2006.01)
(Continued)

(52) U.S. Cl.
CPC ............. *A61B 1/05* (2013.01); *A61B 1/00096* (2013.01); *A61B 1/00098* (2013.01); *A61B 1/00101* (2013.01); *A61B 1/018* (2013.01); *A61B 1/051* (2013.01); *A61B 1/053* (2013.01)

(58) Field of Classification Search
USPC .............. 348/65, 76, 373, 374; 600/101, 160, 600/161
See application file for complete search history.

(56) References Cited

U.S. PATENT DOCUMENTS 4,641,635 A    2/1987   Yabe
5,325,847 A    7/1994   Matsuno
(Continued)

FOREIGN PATENT DOCUMENTS

CN    1080061 A      12/1993
JP    61-059309      3/1986
(Continued)

OTHER PUBLICATIONS

Extended European Search Report dated Jul. 12, 2010.
(Continued)

*Primary Examiner* — Liangche A Wang
*Assistant Examiner* — Cheikh Ndiaye
(74) *Attorney, Agent, or Firm* — Scully, Scott, Murphy & Presser, PC

(57) ABSTRACT

An image-capturing apparatus and a repair method thereof are provided. The image-capturing apparatus includes a lens frame to which one or more lenses are fixed; an image-capturing frame to which an image-capturing device is fixed; and a fixing member for fixing the lens frame and the image-capturing frame to each other without adhering a fitted portion between the lens frame and the image-capturing frame. The repair method for the image-capturing apparatus includes destructing a fixing member for fixing to each other a lens frame to which one or more lenses are fixed and an image-capturing frame to which an image-capturing device is fixed, and releasing fixing between the frames; replacing at least either of the lens frame and the image-capturing frame; and fixing to each other the lens frame and the image-capturing frame.

18 Claims, 25 Drawing Sheets

(51) Int. Cl.
*A61B 1/00* (2006.01)
*A61B 1/018* (2006.01)

(56) References Cited

U.S. PATENT DOCUMENTS

| | | | | |
|---|---|---|---|---|
| 5,379,756 A * | 1/1995 | Pileski et al. | ............... | 600/109 |
| 5,569,157 A | 10/1996 | Nakazawa et al. | | |
| 5,662,588 A | 9/1997 | Iida | | |
| 5,707,344 A | 1/1998 | Nakazawa et al. | | |
| 5,730,701 A | 3/1998 | Furukawa et al. | | |
| 5,865,726 A | 2/1999 | Katsurada et al. | | |
| 6,338,717 B1 | 1/2002 | Ouchi | | |
| 6,370,225 B1 * | 4/2002 | Telymonde | ............... | 378/98.2 |
| 6,390,973 B1 | 5/2002 | Ouchi | | |
| 2001/0007051 A1 | 7/2001 | Nakashima | | |
| 2002/0188177 A1 | 12/2002 | Miyanaga | | |
| 2005/0185088 A1* | 8/2005 | Kale et al. | ............... | 348/374 |

FOREIGN PATENT DOCUMENTS

| | | |
|---|---|---|
| JP | 61-163315 A | 7/1986 |
| JP | H02-114006 U | 9/1990 |
| JP | 09-064330 | 3/1997 |
| JP | 2000-201884 | 7/2000 |
| JP | 2001-207641 A | 8/2001 |
| JP | 2001-346751 | 8/2001 |
| JP | 2002-253484 | 9/2002 |
| JP | 2003-038419 | 2/2003 |
| JP | 2003-230533 | 8/2003 |
| JP | 2004-72526 | 3/2004 |
| WO | WO 2004/036266 A2 | 4/2004 |

OTHER PUBLICATIONS

Chinese Office Action dated Mar. 8, 2010.
Supplementary Extended European Search Report dated Sep. 17, 2009.

* cited by examiner

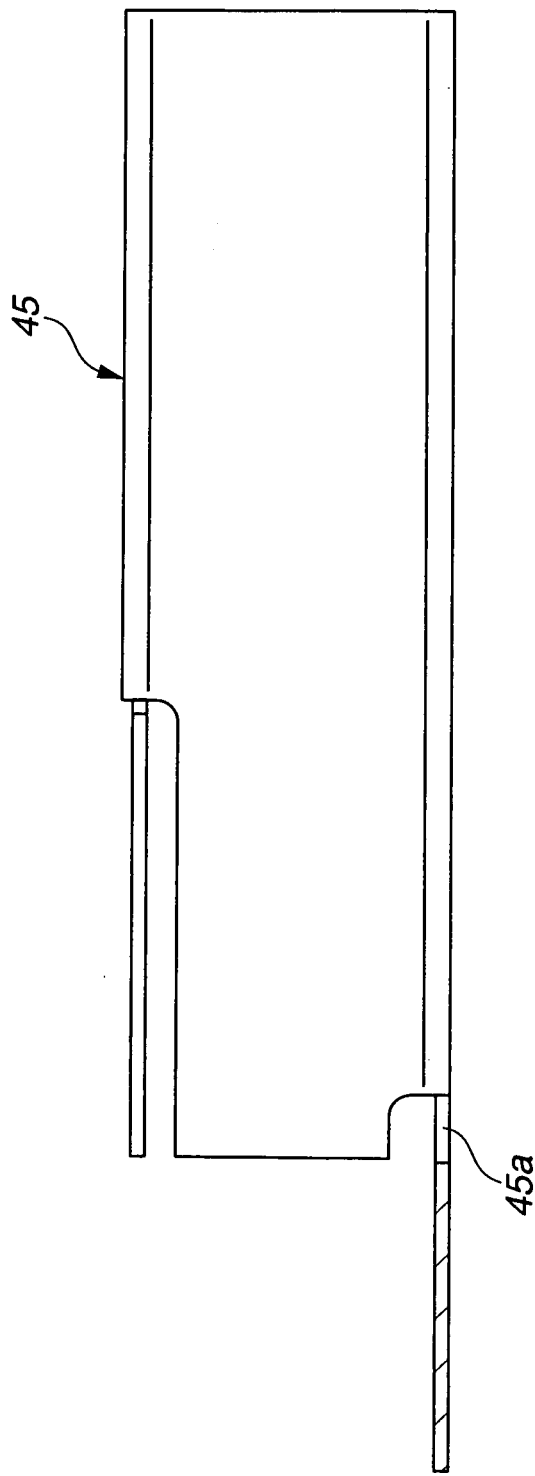

ELECTRONIC ENDOSCOPE

CROSS REFERENCE TO RELATED APPLICATION

This application is a continuation application of PCT/JP2005/012417 filed on Jul. 5, 2005 and claims benefit of Japanese Applications No. 2004-198527 filed in Japan on Jul. 5, 2004 and No. 2005-062926 filed in Japan on Mar. 7, 2005, the entire contents of each of which are incorporated herein by their reference.

BACKGROUND OF THE INVENTION

1. Field of the Invention

The present invention relates to an electronic endoscope applicable for performing treatment using a treatment tool.

2. Description of the Related Art

In recent years, electronic endoscopes whereupon a solid-state image-capturing device is mounted have been widely used in medical fields and so forth. As a first preceding example of an electronic endoscope, for example, Japanese Unexamined Patent Application Publication No. 2003-230533 discloses an endoscope having a lateral view or a rear perspective as the field of vision.

Also, as a second preceding example of an electronic endoscope, for example, Japanese Unexamined Patent Application Publication No. 2004-72526 discloses an electronic endoscope having a channel capable of inserting the treatment tool through, and having lateral view or a rear perspective as the field of vision.

In the above second preceding example, a wedge-shaped lens is used wherein the field of view angle on the upper side is thicker than the field of view angle on the lower side, as a lens on the foremost tip portion of the objective optical system.

Note that with an endoscope with a lateral view or a rear perspective as the field of vision having an erecting block which changes the protruding direction of the treatment tool, an objective optical system and erecting block are adjacently disposed in the left and right directions perpendicular to the lengthwise direction on the tip portion of the insertion portion. Also, with the erecting block disposed in the vicinity of the channel exit, if the tip side of the treatment tool is protruded from the channel exit in the state of the protruding direction being restricted, the tip side of the protruded treatment tool is to be captured in the field of view angle of the objective optical system.

In this case, if the field of view angle of the objective optical system has the base end side of the insertion portion at the upper direction of the field of vision and the tip side of the insertion portion at the lower direction of the field of vision, the objective optical system and erecting block are disposed on the tip portion of the insertion portion so that the tip side of the protruded treatment tool enters in the field of vision on the upper side. Also, in a case of an optical image, which is formed by the objective optical system, being photoelectrically converted by the image-capturing device and displayed on a display device as the endoscope image, relating to the field of vision direction in the center of the objective optical system, this image is displayed so that the base side of the insertion portion is displayed in the upper direction of the observation image and the tip side of the insertion portion is displayed in the lower direction of the observation image. In the case of performing treatment such as ERCP (Endoscopic Retrograde Cholangiopancreatography) for example, using an endoscope with a lateral view or rear perspective having an erecting block which changes the protruding direction of the treatment tool, the erecting block is operated to change the protruding direction of the treatment tool, and a procedure is performed to insert a catheter from the duodenal papilla to the bile duct (or pancreatic duct). When performing such treatment, the treatment tool having changed the protruding direction by the erecting block is set for the tip thereof to be displayed on the upper half of the observation image which the surgeon observes.

SUMMARY OF THE INVENTION

The present invention provides an electronic endoscope comprising: an insertion portion for being inserted into a body cavity, wherein a channel through which a treatment tool is inserted is provided; a tip portion main body provided on the tip of the insertion portion; an erecting device provided on the tip portion main body, disposed in the vicinity of the channel tip opening, and capable of changing the protruding direction of the treatment tool protruding from the tip opening; a solid-state image-capturing device provided on the tip portion main body for image-capturing an image within the body cavity as an endoscope image; an objective optical system provided on the tip portion main body, having a predetermined field of view angle in the field of vision direction at least 90 degrees from a line segment defined in the direction from the base end to the tip of the insertion portion, for capturing an image within the body cavity including the treatment tool protruding from the tip opening with a first field of view angle equating to the upper field of view angle during observation, wherein the base side of the insertion portion is the field of vision range as the center of the field of vision direction in the field of view angle, and forms this image at the solid-state image-capturing device; and field of view angle setting means for setting a second field of view angle equating to the lower field of view angle during observation, wherein the tip side of the insertion portion of the field of vision range with the field of vision direction as the center of the field of view angle, and setting the first field of view angle to be the same or smaller than the second field of view angle.

BRIEF DESCRIPTION OF THE DRAWINGS

FIG. 8A is a side face view showing the configuration of the frame body of a solid-state image-capturing unit.

FIG. 10 is a configuration diagram of an electronic endoscope wherein an image-capturing device according to a first modification is built in.

DETAILED DESCRIPTION OF THE PREFERRED EMBODIMENTS

The embodiments of the present invention will be described below with reference to the diagrams.

First Embodiment

A first embodiment of the present invention will be described below with reference to FIGS. 1 through 30.

Figure 1:
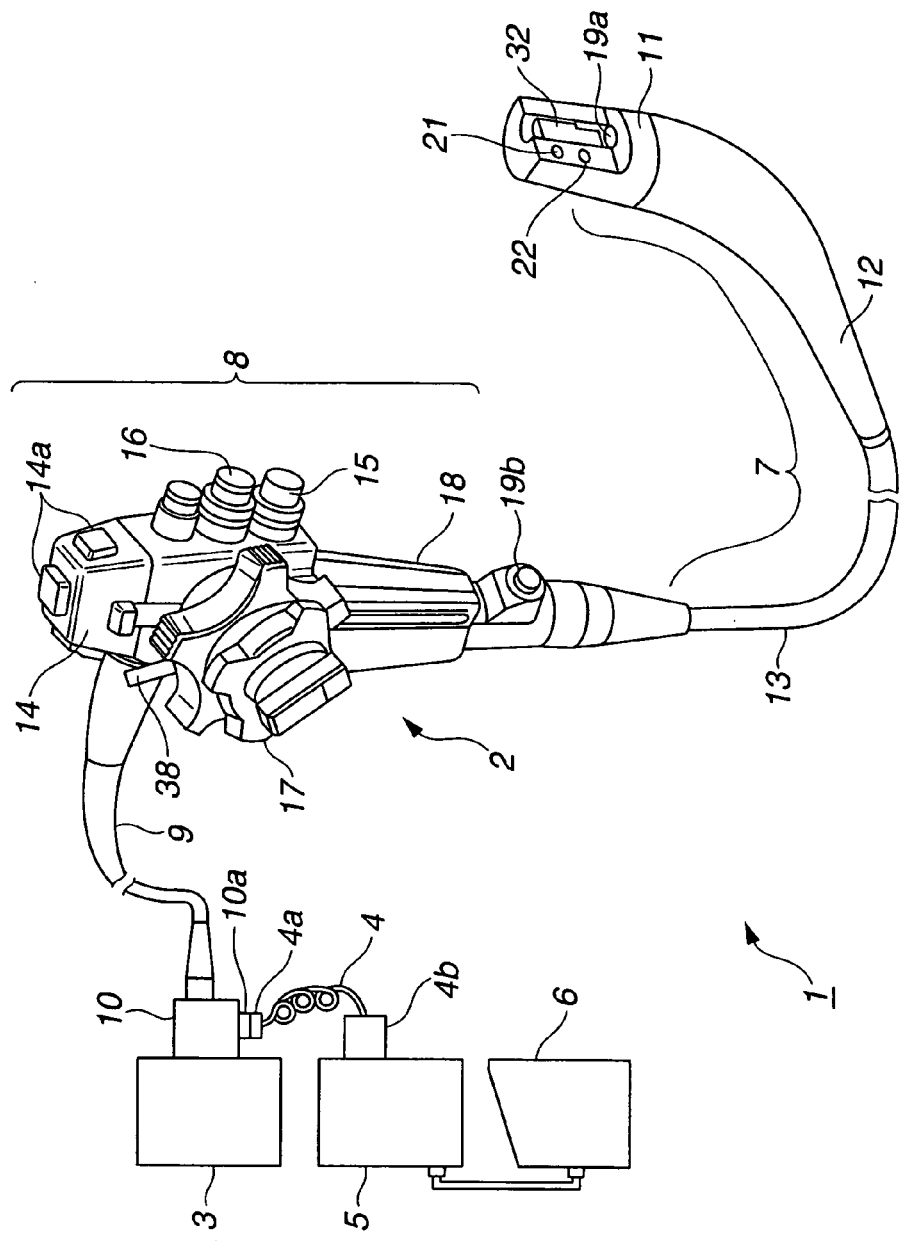
FIG. 1 is a configuration diagram of an electronic endoscope system with a first embodiment according to the present invention.

The electronic endoscope system 1 shown in FIG. 1 comprises an electronic endoscope 2 configuring the first embodiment, a light source device 3 for supplying illumination light by being connected to the electronic endoscope 2, a video processor 5 which is connected to the electronic endoscope 2 via a scope cable 4 and which houses a signal processing circuit for performing signal processing for an image-capturing device 26 (see FIG. 4) housed within the electronic endoscope 2, and a monitor 6 which displays a video signal inputted via a monitor cable connected to the video processor 5 on a display screen with a color display.

This electronic endoscope 2 has a slender and flexible insertion portion 7 which is inserted within a body cavity and so forth, an operating unit 8 formed on the base side of the insertion portion 7, a universal cord portion 9 extending from the operating unit 8, and a scope connector portion 10 which is provided on the end portion of the universal cord portion 9 and which is detachably connected to the light source device 3.

A connecting point connector portion 10a is provided on the side portion of the scope connector portion 10, and the other end of the scope cable 4 provided with an electric connector 4a which is detachable from this connecting point connector portion 10a is detachably connected to the video processor 5 by the electric connector 4b.

The insertion portion 7 comprises a tip portion 11 whereupon is provided an image-capturing device 26 (described later with reference to FIG. 2), a bendable bending portion 12 formed on the base side of the tip portion 11, and a long flexible tube portion 13 which reaches from the base side of the bending portion 12 to the tip side of the operating unit 8.

A switch portion 14 having multiple switches 14a provided thereupon is provided on the topmost portion of the operating unit 8. Also, an air/water transporting control unit 15 for control of transporting air/water, and a suction control unit 16 for controlling suction are provided on the side face of the operating unit 8. The operating unit 8 further has a bending operation knob 17, and the user can bend the bending portion 12 by gripping a gripping portion 18 on the tip side of the operating unit 8 to operate the bending operation knob 17.

Also an unshown air/water transportation tube is inserted in the insertion portion 7, and this air/water transportation tube is connected to the air/water transportation control unit 15 with the operation unit 8. Further, the air/water transportation tube inserted in the universal cord portion 9 has the tail end thereof reaching the scope connecter portion 10, and thus is connected to an air/water transportation mechanism in the light source device 3.

Also, the treatment tool tube (also called a channel) 19 (see FIG. 3C) for inserting in the treatment tool and for performing suction, which is inserted in the insertion portion 7, is divided into two branches near the front end of the operating unit 8 at the rear side of the channel, wherein one branch is communicated to the treatment tool insertion opening 19b, and the other is communicated to the suction tube within the universal cord portion 9 via the suction control unit 16. This suction tube reaches an unshown suction cap of the scope connector portion 10.

Also this channel 19 is communicated to a tip opening 19a which opens at the tip portion 11, and during suction operation suctions bodily fluids and so forth from the tip opening 19a. In the event that a treatment tool such as a forceps (cannula) and so forth is inserted from the treatment tool insertion opening 19b, the tip side thereof is the treatment tool exit for protruding therefrom.

Also, a light guide 20 (see FIG. 20) for transmitting light is inserted in the insertion portion 7, operating unit 8, and universal cord portion 9, whereby the base side of the light guide 20 reaches the scope connector portion 10. This light guide 20 transmits illumination light supplied from a lamp within the light source device 3. Then the transmitted illumination light is emitted in the front of the tip face of the illumination lens 21 (the side portion of the insertion portion 7), via the illumination lens 21 attached nearer the illumination window from the tip face fixed to the tip portion 11, and subject such as an affected portion and so forth is illuminated.

Figure 2:
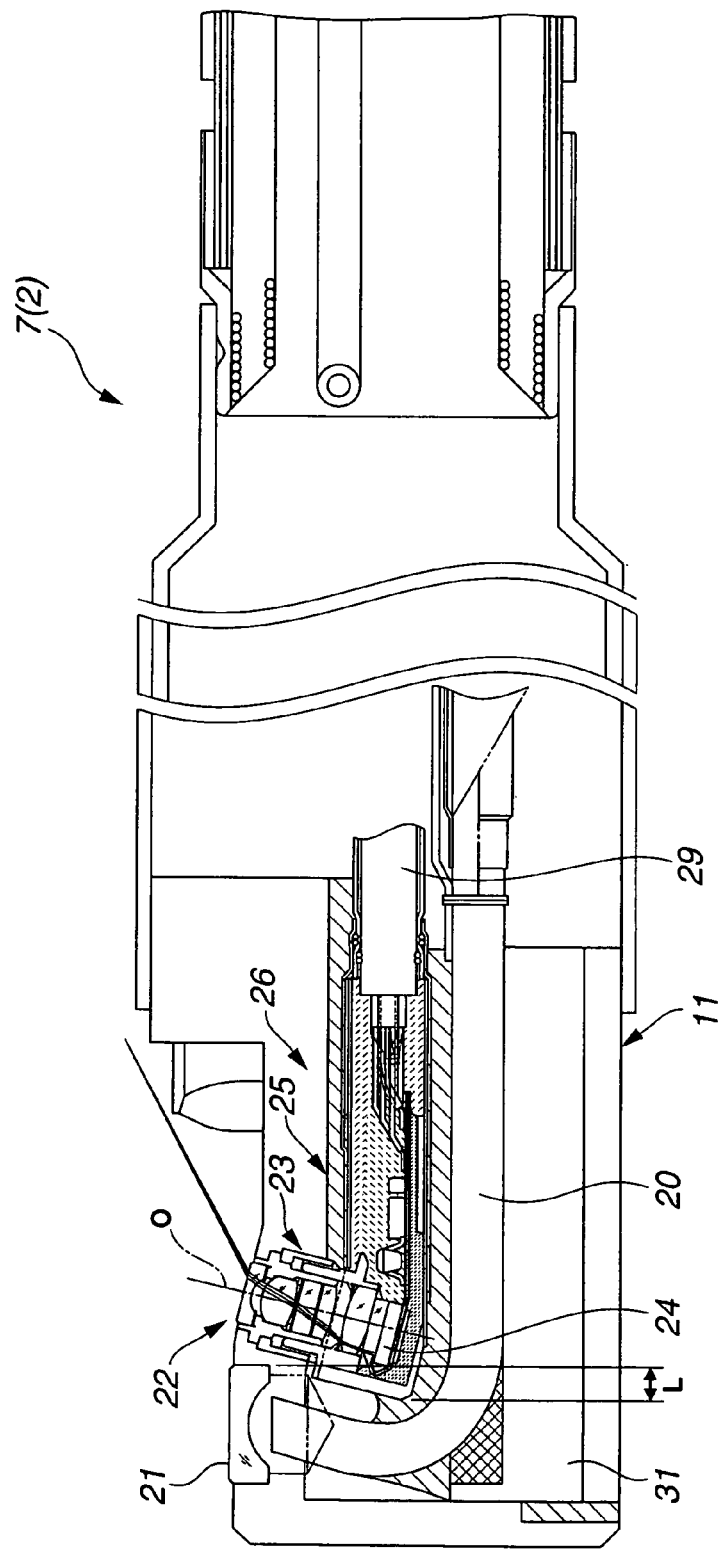
FIG. 2 is a diagram showing a cross-sectional configuration of primary portions of an insertion portion of an electronic endoscope.

As shown in FIG. 2, the tip portion 11 has a flat surface in a generally cylindrical shaped side face portion cut out from the tip and formed to face the side direction, whereupon this flat surface has the illumination window and an observation window provided adjacent to one another in the lengthwise direction on the insertion portion 7.

This observation window has an objective optical system unit 23 wherein the objective optical system 22 is built in, attached thereto. Also, on the base side of the objective optical system unit 23, a solid-state image-capturing unit 25 whereupon a charge-coupled device (abbreviated as CCD) 24 serving as a solid-state image-capturing device is mounted is attached thereto. The image-capturing device 26 for image-capturing a subject is formed with the objective optical system unit 23 and the solid-state image-capturing unit 25.

Then the optical image of the subject illuminated with the illumination light emitted from the illumination lens 21 is image-captured onto an image-capturing screen of the CCD 24 by the objective optical system 22, and with the CCD 24, photoelectric conversion is performed. This CCD 24 is implemented in the TAB (Tape Automated Bonding) tape 27 stored within the solid-state image-capturing unit 25. An electronic part 28 such as a transistor, condenser, or the like is also implemented in this TAB tape 27. A signal cable 29 is connected to the rear side of this TAB tape 27.

This signal cable 29 is inserted in the insertion portion 7 to be connected to the video processor 5 via the scope cable 4 illustrated in FIG. 1. Then a video signal is generated from the image-capturing signal image-captured with the CCD 24, through the signal processing circuit within the video processor 5, and this video signal is inputted to the monitor 6.

Figure 3A:
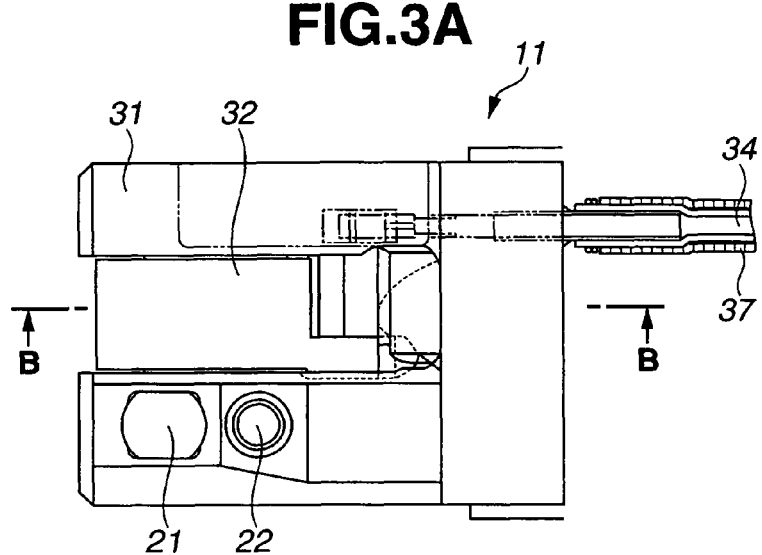
FIG. 3A is a plan view of the configuration in the vicinity of a tip portion viewed from the side of the insertion portion in FIG. 2.

A plan view of the tip portion 11 as seen from the upper side of the paper in FIG. 2 is shown in FIG. 3A. As shown in FIG. 3A, the vicinity of the center adjacent to the illumination window and observation window on the tip portion main body 31 configuring the tip portion 11 has a treatment tool erecting block (hereafter simply referred to as erecting block) 32 disposed thereupon which is carved out from the tip side and configures the erecting device.

Also, adjacent to this erecting block 32 (on the opposite side as the illumination window and observation window adjacent thereto), a erecting drive mechanism 33 for erecting the erecting block 32 is disposed, and an erecting device is formed on the erecting block 32 and the erecting drive mechanism 33.

Figure 3B:
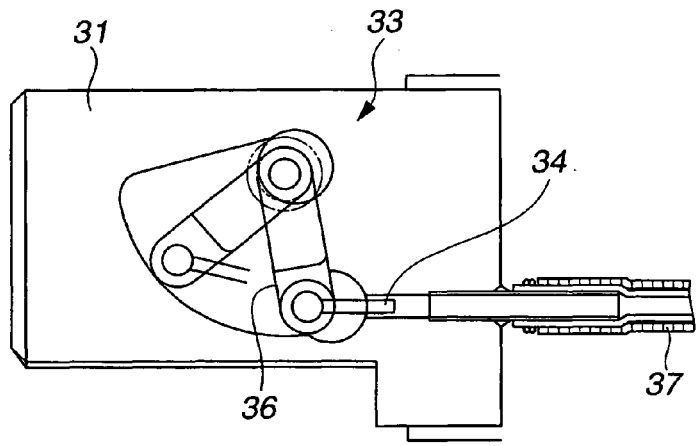
FIG. 3B is a diagram showing an erecting block driving mechanism provided on the tip portion of the insertion portion.
Figure 3C:
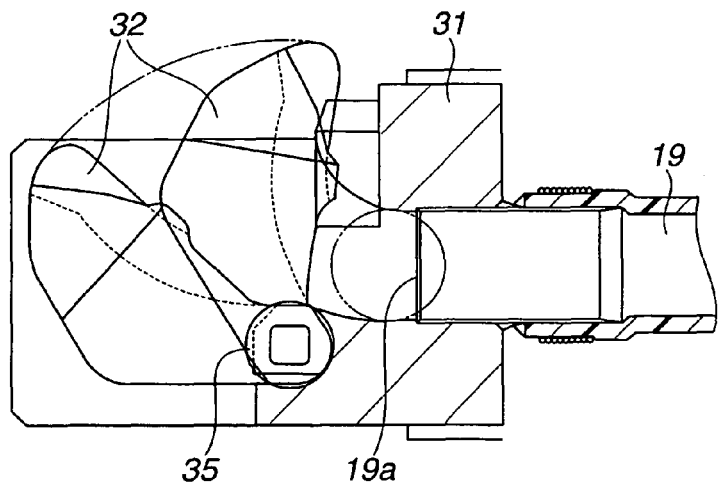
FIG. 3C is a cross-sectional view of the configuration in the vicinity of the tip of a channel for insertion of a treatment tool.

This erecting drive mechanism 33 is linked to a wire 34 for transmitting force for erecting. With this erecting drive mechanism 33, as shown in FIGS. 3B and 3C, the erecting block 32 is supported so as to be rotatable (erectable) by the erecting block shaft 35 (as a rotation axis) 35. Also, this erecting block 32 has a shaft and link 36 attached thereto for the purpose of applying erecting force.

Also, this link 36 is linked to a wire 34 via a connecting member, and by advancing/retreating the wire 34, the erecting block 32 can be erected, as show in FIG. 3C. Note that FIG. 3B shows the schematics of the operation for erecting, viewed from the side in FIG. 3A, and FIG. 3C shows a cross-sectional configuration of the vicinity of the erected erecting block to be erected with a B-B cross-section in FIG. 3A.

The wire 34 is inserted in a tube 37 for inserting wires, wherein the trailing end of the wire 34 is connected to an erecting operation knob 38 provided on the operating unit 8 in FIG. 1.

Then, by performing an operation to rotate the erecting operating knob 38, the user can advance/retreat the wire 34 to erect the erecting block 32 or cause the erecting block to be in a non-erected state. In other words, by operating the erecting operating knob 38, the user can adjust the erecting angle of the erecting block 32 to a desired angle. By changing the erecting angle of the erecting block 32, the protruding direction of the restricted treatment tool can be changed. Note that as described later with reference to FIG. 29, with the present embodiment, the position of the erecting block shaft 35 is provided so as to be shifted farther toward the tip side of the insertion portion 7 than in the case of the preceding example, and therefore, enables the tip side of the treatment tool in the case of setting the erecting block to the greatest erecting angle to be captured within the observation field of vision in a sure manner.

Figure 4:
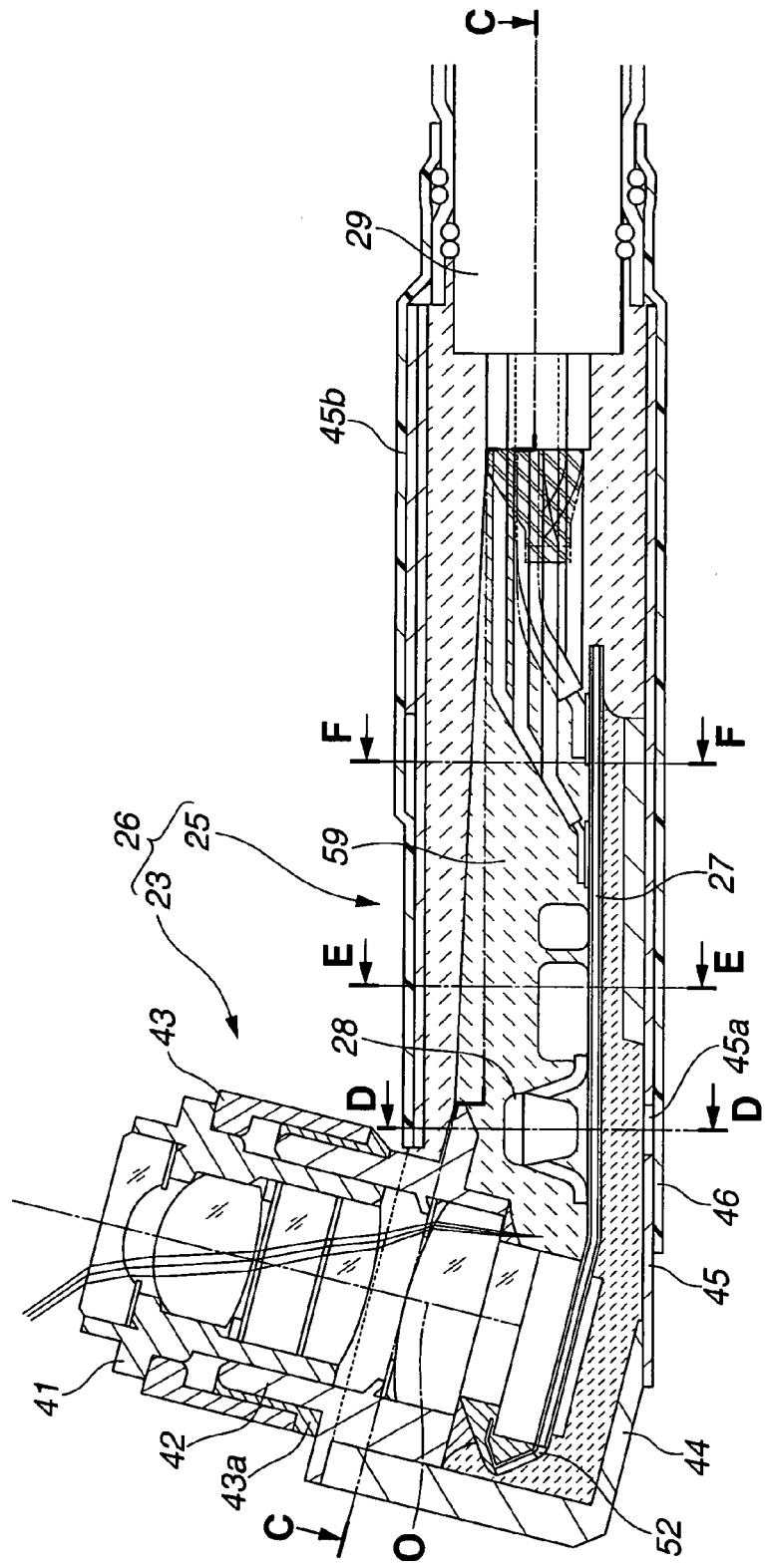
FIG. 4 is a cross-sectional view showing the cross-section of the configuration of the entire image-capturing device.

An enlarged view of a portion of the image-capturing device 26 illustrated in FIG. 2 is shown in FIG. 4.

As shown in FIG. 4, a front lens system of the objective optical system 22 is attached to a first lens frame 41, and also a back lens system is attached to a second lens frame 42, these lens frames 41 and 42 being linked so as to fit together.

Also, with the present example, the tip is externally fit to the first lens frame 41, a connecting frame 43 which covers the periphery of the portions where the two lens frames 41 and 42 fit together is provided, and the two lens frames 41 and 42 are reinforced with the connecting frame 43. Also, in this case, the fitted portion of the first lens frame 41 and the connecting frame 43 are adhesively fixed. A stepped portion is provided on the second lens frame 42, and adhesive 43a is filled in the inner side of the connecting frame 43 and in the space on the lower side thereof, such that the connecting frame 43 is fixed by adhesion to the second lens frame 42, thereby determining the positions of the front lens system and the back lens system of the objective optical system 22. The image-capturing device 26 is positioned based on an abutting portion of the first lens frame 41 as to the tip portion main body 31 and the fitted portion of the connecting frame 43.

Figure 6A:
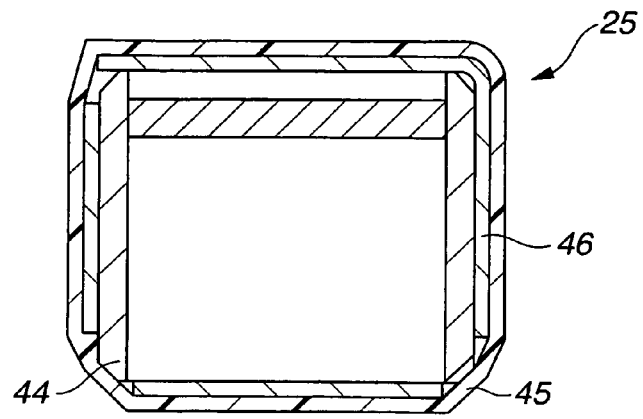
FIG. 6A is a cross-sectional view of the D-D line in FIG. 4.

Also, the back end of the lens frame 42 is linked to the perimeter of the CCD 24 disposed on the tip side of the solid-state image-capturing unit 25 and to an image-capturing frame 44 wherein a TAB tap 27 whereupon an electronic part 28 disposed on the back end side thereof is stored. The bottom portion of the image-capturing frame 44 is cut out and is linked by being shielded by a metallic shield frame 45 having a shielding function in a generally cylindrical shape, as shown in FIG. 6A and so forth, and in FIGS. 8A and 8B. This shield frame 45 is extended toward the back side farther back than the image-capturing frame 44, and also covers the connection portion on the tip side of the signal cable 29 which is connected to the TAB tape 27.

Figure 8B:
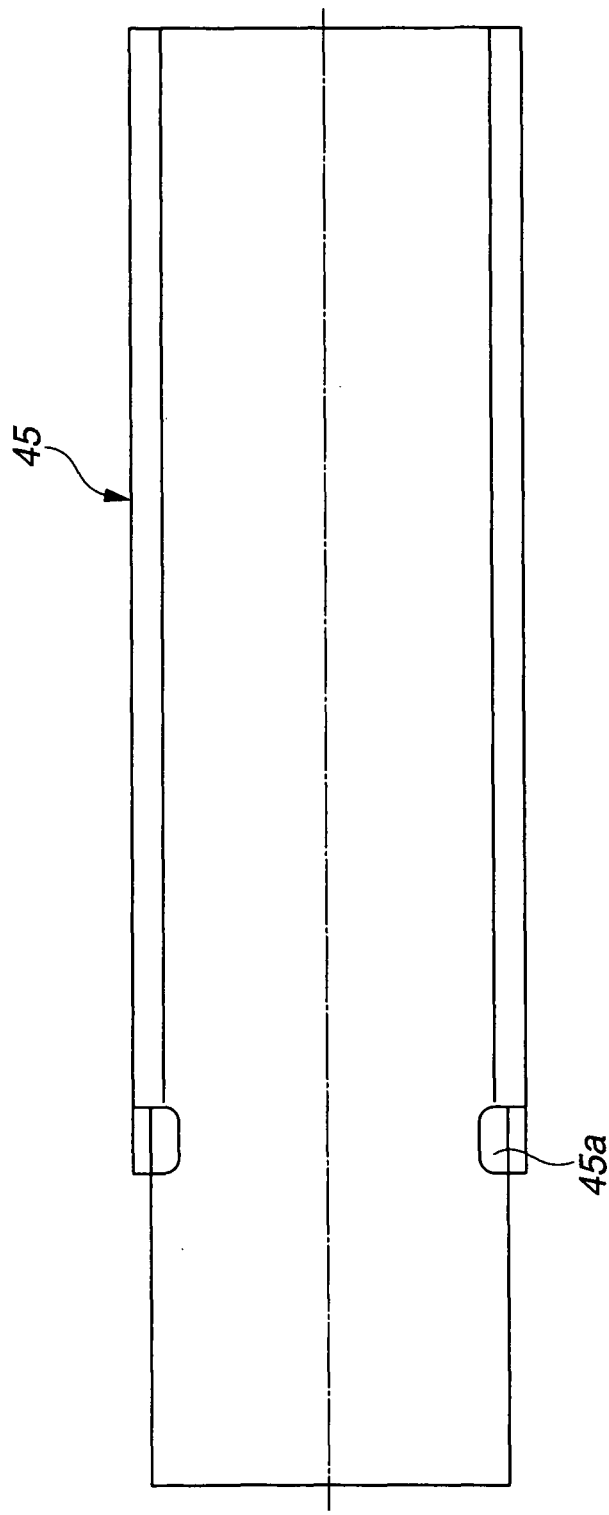
FIG. 8B is a bottom face view showing the configuration of the frame body of a solid-state image-capturing unit.

Also, this shield frame 45 is covered with a heat-shrunk tube 46. Note that FIG. 8A shows a side face view of the shield frame 45, and FIG. 8B shows the bottom face view thereof.

This shield frame 45 which is made to be thin, has the bottom side thereof protruding toward the front, and this protruding portion is linked to the bottom portion which is cut diagonally with the image-capturing frame 44, as shown in FIG. 4. Thus by cutting the back end of the bottom portion diagonally with the image-capturing frame 44, the size in the height direction (side view direction) can be shortened.

Also, in the position shown with the D-D line cross-section in FIG. 4, an opening 45a is formed on the bottom face of the shield frame 45. This is for the purpose of widening the horizontal width of the protruding portion on the bottom side so as to be wider than the horizontal width of the tube portion on the back end side (see FIG. 6B), and for stabilizing the shape of the protruding portion when bending to form a shape (so as not to have a bending curvature). Then as shown in FIG. 4, the tip is cut diagonally, and by the bottom side (rather than the top side) covering the opening 45a with a heat-shrunk tube 46 in a forward-protruding shape, the opening 45a is covered, and a water-tight functionality thereof is secured.

Figure 6B:
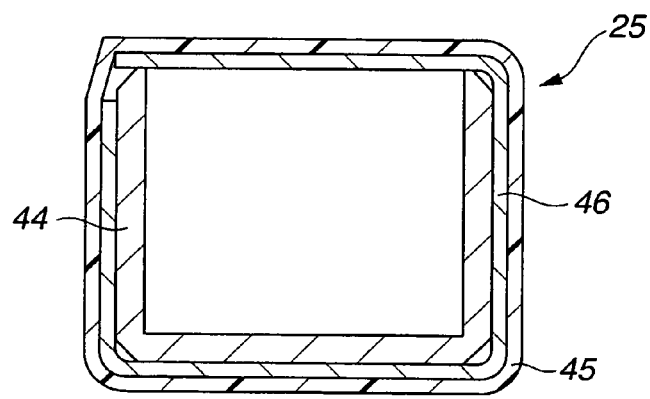
FIG. 6B is a cross-sectional view of the E-E line in FIG. 4.
Figure 6C:
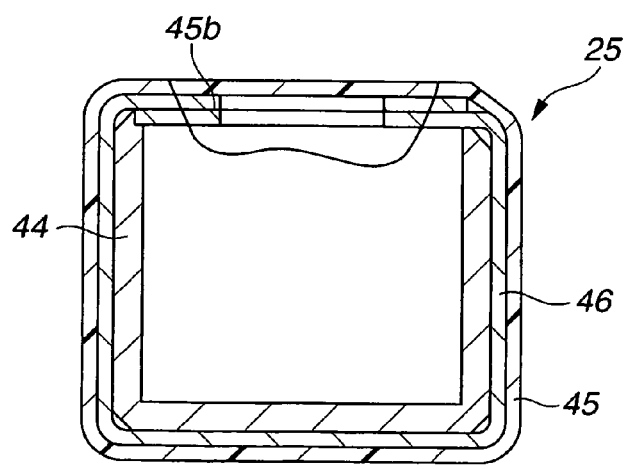
FIG. 6C is a cross-sectional view of the F-F line in FIG. 4.

Also, this shield frame 45 has a configuration wherein the approximately back half has provided a stacking portion 45b wherein the upper portion is folded over to be stacked so as to be doubled (see FIG. 4), thus improving upon the strength thereof, as shown in FIGS. 4, 6B, and 6C. Also, the front side is in a shape easily processed without folding over (as with the case with the back side), as well in an arrangement completely covering the upper portion of the image-capturing frame 44 (even if the parts dimensions are scattered).

Note that the axis of the objective optical system 22 is formed so as to lean slightly farther towards the back than the side orthogonal to the axial direction of the insertion portion 7, as shown in FIGS. 4 and 2, and the lens frames 41 and 42 attached to the objective optical system 22 are also disposed along the axis, wherein the image-capturing frame 44 attached to the back end of the lens frame 42 protrudes farther toward the tip side than the lens frame 41. In the case of FIG. 4, the image-capturing optical axis O to be described later and the axis of the objective optical system 22 match approximately. Note that with the present description, an axis of the objective optical system 22 and the lens configuring this is defined as having passing through the center thereof.

The tip side of the light guide 20 disposed adjacent to the tip side of the image-capturing device 26 is bent to an angle greater than 90 degrees, and a portion on the tip side protruding (towards the tip side) of the image-capturing device 26 is disposed so as to enter into the space formed by such bending.

By disposing thus, the length of the rigid portion of the tip portion main body 31 is compressed to be shorter. In the example shown in FIG. 2, the tip portion of the image-capturing frame 44 is positioned toward the tip side only the amount shown by the distance L than the position at the back end of the illuminating lens 21. In other words, the illuminating lens 21 for emitting illumination light is disposed adjacent to the image-capturing device 26, this image-capturing device 26 being disposed so that at least a portion of the image-capturing device 26 enters into a region wherein the surface of the illumination lens 21 projects in a direction perpendicular to the lengthwise direction of the insertion portion 7.

With the preceding example, the length of the rigid portion of the tip is long, but with the present configuration, the objective of shortening the distance of the lengthwise direction between the image-capturing device 26 and the insertion portion 7 of the illumination lens 21 and thus shortening the length of the rigid portion of the tip can be achieved.

Figure 5:
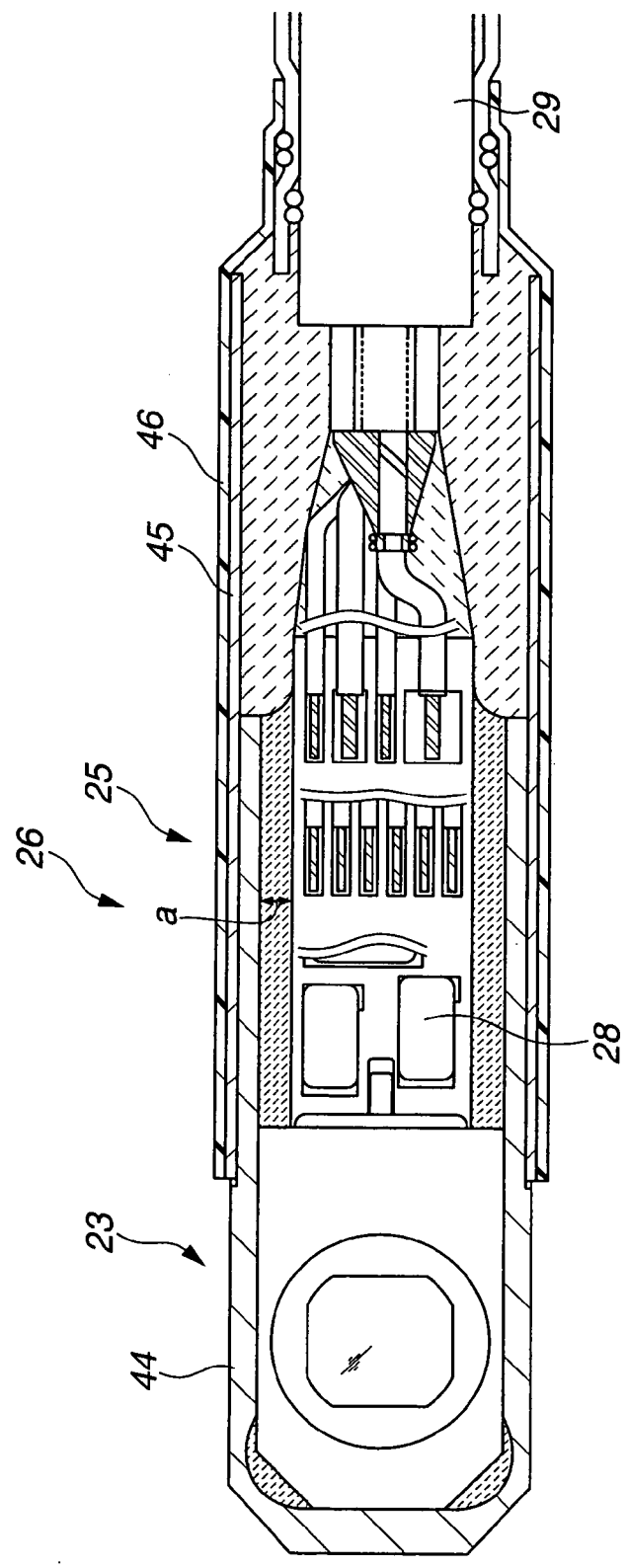
FIG. 5 is a cross-sectional view of the C-C line in FIG. 4.

Also, the width of the TAB tape 27 disposed within the image-capturing frame 44 is set to have a dimension with an appropriate clearance a as to the width of the image-capturing frame 44, as shown in FIG. 5. In other words, even in the case that the CCD 24 stores the TAB tap 27 mounted which the position thereof is shifted within a restricted range (horizontal direction, rotational direction) as to the image-capturing frame 44 having secured this clearance, the variance in angles of leaning of the image to be image-captured (the rotational angle around the center axis of the image-capturing face) can be kept below the value deemed necessary.

Generally in the case of a medical-use electronic endoscope, performing anti-bacterial processing in a sure manner for a used endoscope is an absolute necessity for preventing contagious diseases and so forth. When disinfecting or sterilizing with a cleaning solution, there are disadvantages in that the disinfecting work is cumbersome, and the solution disposal process of the cleaning solution requires a great expense.

Thus, recently, a high pressure high temperature steam sterilization (such as autoclave) which is not accompanied by cumbersome work has become prevalent for use with endoscope devices, particularly for rigid scopes.

Particularly with electronic endoscopes, even if a small amount of moisture, such as humidity, enters the tip portion, there is the concern that fogging can occur from the inner side on the objective optical system, and the solid-state image-capturing device or the substrate and so forth mounting electronic parts which processes signals from the solid-state image-capturing device can become corroded or short-circuits, and the image quality of endoscope images obtained in such a state declines significantly.

Thus, various means for preventing moisture from entering the image-capturing unit formed with an objective optical system and solid-state image-capturing device and substrate, and for preventing deterioration of the configuration members have been proposed.

However, conventionally, there are no proposals having considered repair or replacement of the image-capturing unit. For example, with Japanese Unexamined Patent Application Publication No. 2000-201884, a configuration is used wherein a lens frame fixedly attached to an objective optical system is fit into the inner circumferential face of the CCD fame fixedly attached to the CCD, and after performing high-precision axis matching, an adhesive and so forth is used to effect airtight linking and fix thereto.

With this configuration, for example in order to performing replacement of the objective lens within the lens frame, a user attempts to remove the lens frame and the CCD frame mutually. Thus, when the adhesive is to be peeled off, damage occurs to the attached face around the CCD frame. In the event of adhesively fixing a CCD frame with such damage and a new lens frame, a highly precise optical matching is impossible due to the damage on the attaching face. In other words, optical functionality and focusing deteriorates.

In other words, there is a disadvantage in that an objective lens or CCD which has been disassembled once cannot be reused, and even in the case wherein only one of the objective lens or CCD is defective, the entire unit must be replaced.

Thus, it is an object to provide an image-capturing device which enables reuse of parts before replacement even in the event of repair/replacement of the image-capturing unit, and so the electronic endoscope 2 shown in FIG. 1 along with the electronic endoscopes to be described below will be described, as well as the image-capturing devices mounted thereupon.

First, an electronic endoscope of a first modification will be described with reference to FIG. 10.

Figure 10:
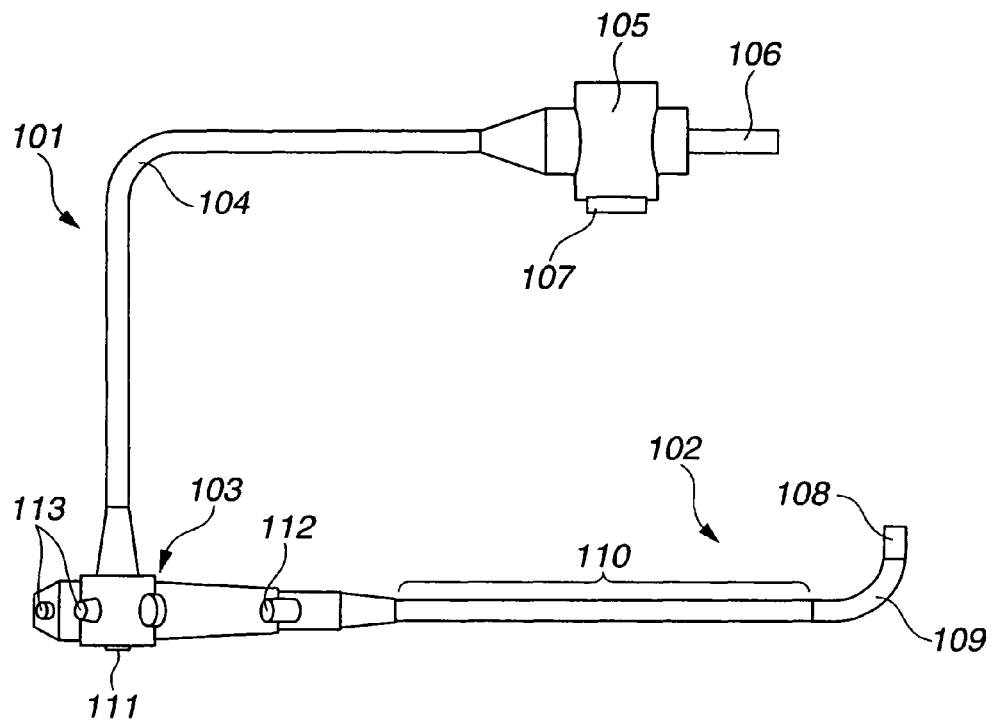

The electronic endoscope 101 shown in FIG. 10 has a slender insertion portion 102, an operating portion 103 formed integrally with the near side of the insertion portion 102 for a surgeon to grip the unit and perform various operations, and a universal cord 104 extended from the operating portion 103. On the other end of the universal cord 104 a connector portion 105 is provided, whereby an unshown light source device or CCU (camera control unit) can be connected to the connector portion 105.

Figure 11:
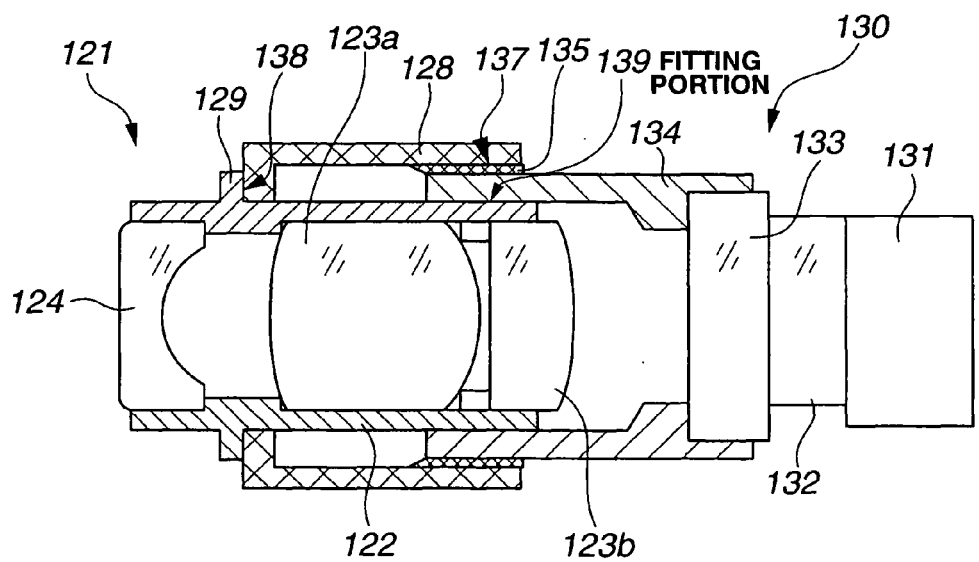
FIG. 11 is a cross-sectional view showing the cross-section of the configuration of the image-capturing device with the first modification.
Figure 12:
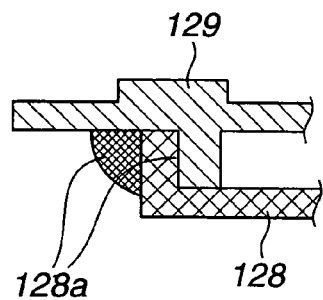
FIG. 12 is an explanatory diagram for describing adhesive of a fixing member.
Figure 13:
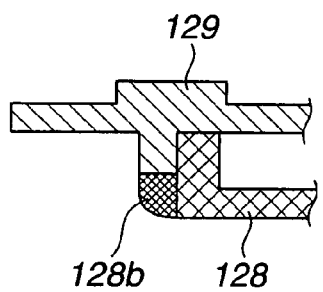
FIG. 13 is an explanatory diagram for describing adhesive of the fixing member.

A bending operation lever 111 and a treatment tool insertion slot 112 for inserting a treatment tool such as a forceps is provided on the operating portion 103. Also, the insertion portion 102 is configured with a flexible tube 110 having flexibility connected to the operating portion 103, a bending portion 109 connected to the tip of the flexible tube, and a tip portion 108 connected to the tip of the bending portion 109. The image-capturing device in FIG. 11 is disposed on the tip portion 108. Note that in addition to the image-capturing device in FIG. 11, an unshown light guide fiber and so forth for transmitting illumination light is also disposed on the tip portion 108.

The image-capturing device in FIG. 11 is configured with an objective lens unit 121 which is an observation optical system and an image-capturing unit 130 serving as image-capturing means. The objective lens unit 121 disposed on the tip of the image-capturing device has an optical window member 124 provided on the front face thereof. The optical window member 124 is configured to be exposed to the tip external surface of the tip portion 108 of the electronic endoscope 101, and for example is configured with a concave shape lens made of sapphire. The concave shape lens is shaped with a flat front side surface (bottom face) and the base side surface thereof is in a concave shape.

The optical window member 124 is attached to the lens frame 122. The lens frame 122 is in a cylindrical shape wherein the tip side and the base side are open. The optical window member 124 is fit into the tip side inner circumferential face of the metallic lens frame 122, and the external circumference of the optical window member 124 and the tip side internal circumference of the lens frame 122 are fixed in an airtight manner. For example, these are fixed with an adhesive such as an epoxy-type, or by soldering.

Also, lenses 123*a* and 123*b* are disposed from the tip side on the lens frame 122. The respective lenses 123*a* and 123*b* are each adhesively fixed to the inner circumference of the lens frame 122 with an adhesive coating over the entire periphery. The lens frame 122 has a protruding portion on the inner circumferential face, and so assembly is arranged such that the optical window member 124 is inserted from the tip side of the lens frame 122, and the lenses 123*a* and 123*b* are inserted from the base side of the lens frame 122.

On the base side of this objective lens unit 121 is disposed with the image-capturing unit 130. The image-capturing unit 130 has a CCD 131 serving as a solid-state image-capturing device, a glass lid 132, and a cover glass 133. The CCD 131 converts an optical image of a subject entered via the objective lens unit 121 into an electric signal. On the base side of the CCD 131, an unshown TAB (Tape Automated Bonding) member is provided, and is electrically connected with an unshown cable inserted through to the electronic endoscope 101 base side. With this cable, a driving signal can be supplied to the CCD 131, and also an image signal is transmitted from the CCD 131.

A glass lid 132 is adhered to the CCD 131 with a UV adhesive or the like, so as to cover the unshown image-capturing face configuring a pixel portion. The glass lid 132 further has a cover glass 133 in a round flat shape which is adhesively fixed thereupon in a state of being pushed out toward the pixel portion center. In other words, the CCD 131, glass lid 132, and cover glass 133 are integrally adhesively fixed.

The cover glass 133 fixed to the CCD 131 is attached to a CCD holding frame 134 serving as an image-capturing frame. The CCD holding frame 134 is in a cylindrical shape wherein the tip side and base side thereof are open, and the cover glass 133 is fit on the inner circumferential face of the base side, and fixedly adhering the external circumferential face of the cover glass 133 and the inner circumferential face of the CCD holding frame 134 with an unshown adhesive.

The lens frame 122 and the CCD holding frame 134 are arranged so as to fit together mutually. Fitting refers to having a clearance of 0.005 mm to 0.03 mm. In other words, the outer diameter of the lens frame 122 and the inner diameter of the CCD holding frame 134 is generally the same, and the base side of the lens frame 122 is fitted into the tip side inner circumferential face of the CCD holding frame 134. Thus, the axis of the objective lens unit 121 and the axis of the image-capturing unit 130 can be matched.

With the present first modification, in the event of linking the lens frame 122 and CCD holding frame 134, an adhesive or the like is not used on the attached face (fitting portion) 139 which mutually make contact with the base side external circumferential face of the lens frame 122 and the tip side inner circumferential face of the CCD holding frame 134. With the first modification, for mutually fixing the lens frame 122 and CCD holding frame 134, a fixing member 128 having an attaching function is used.

The fixing member 128 is a cylindrical member wherein the front face is open on the base side thereof, and the rear side is open with a predetermined diameter, wherein the base side inner diameter is slightly larger than the external diameter of the CCD holding frame 134. The clearance is set to be larger than the fitting clearance mentioned above. For example, this clearance can be set to be greater than 0.03 mm. Regarding the fixing member 128, a material which is at least more flexible than the CCD holding frame 134 is used, such as a plastic or acetal resin may be used, for example. Also, regarding the fixing member 128, a material which is more flexible than the lens frame 122 should be used. Also, if the CCD holding frame 134 or the lens frame 122 is made of stainless steel, the fixing member 128 may be configured with brass.

The tip side opening of the fixing member 128 is formed to a size attachable to the outer circumferential face of the lens frame 122. A protruding portion 129 is formed in predetermined positions on the external circumferential face of the lens frame 122 from the tip, the tip face of the fixing member 128 is abutted against this protruding portion 129, and the adhering portion 138 of the tip face and the base side face of the protruding portion 129 is adhesively fixed with an unshown adhesive, for example an epoxy-type adhesive is used. Thus, the protruding portion 129 also becomes means for determining the position of an unshown scope and image-capturing device and for determining the position of the fixing member 128 and lens frame 129.

Note that the joining face of the tip inner circumferential face of the fixing member 128 and the external circumferential face of the lens frame 129 may also be adhesively fixed with an adhesive. In this case, for example, adhesive fixing with an adhesive 128a such as that shown in FIG. 12 can be used, so the adhesive area is wider and thus enables stronger fixing. Also, as in FIG. 13, the circumference face of the protruding portion 129 and the tip face of the fixing member 128 can be fixed with an adhesive 128b. In this case, by peeling off the adhesive, the objective lens can be reused.

With the present first modification, upon the fixing member 128 being adhesively fixed to the objective lens unit 121, the CCD holding frame 134 is inserted in the base side inner circumferential face of the fixing member 128. Then while performing axis-matching and focal point-matching, the space (adhesive portion 137) between the inner circumferential face of the fixing member 128 and the outer circumferential face of the CCD holding frame 134 is filled with an adhesive 135, and these are adhesively fixed while determining the position of each.

With the assembly of the first modification thus configured, first the optical window member 124 and the lenses 123a and 126 are fixedly attached to the lens frame 122, then the integrally configured CCD 131, glass lid 132, and cover glass 133 are fixedly attached to the CCD holding frame 134. Then, the fixing member 128 is adhesively fixed on the outer circumferential side of the lens frame 122 with the adhesive portion 138 of the protruding portion 129.

In this state, the lens frame 122 is fitted in the tip side inner circumferential face of the CCD holding frame 134. Adhesive is not coated on both fitting portions 139. High precision axis matching can be performed by fitting together the CCD holding frame 134 and the lens frame 122 according to the dimension precision of the inner diameter of the CCD holding frame 134 and the external diameter of the lens frame 122.

With this fitting process, the CCD holding frame 134 is inserted into the fixing member 128. Next, the space (adhesive portion 137) between the external circumference face of the CCD holding frame 134 and the inner circumferential face of the fixing member 128 is filled with an adhesive 135, and upon performing focal point matching, is adhesively fixed. Thus, an image-capturing device configured with an objective lens unit 121 and an image-capturing unit 130 is obtained. Here, the objective lens unit 121 and the CCD holding frame 134 can be disassembled for the purpose of repair or replacement. In this case, the adhesive 135 of the adhesive unit 137 wherein the external circumferential face of the CCD holding frame 134 and the inner circumferential face of the fixing member 128 are facing is peeled off.

Figure 14A:
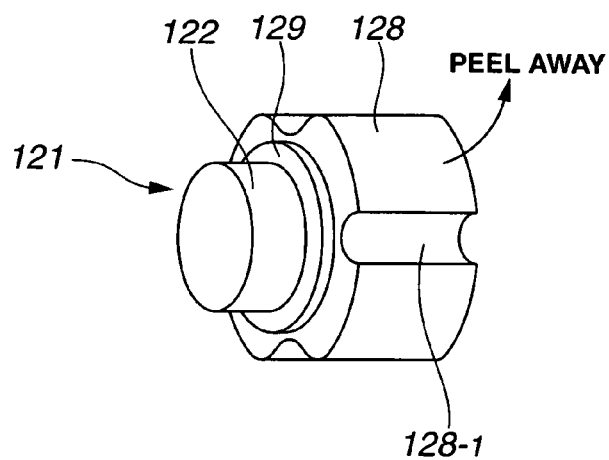
FIG. 14A is an explanatory diagram showing the fixing member attached to a lens frame.
Figure 14B:
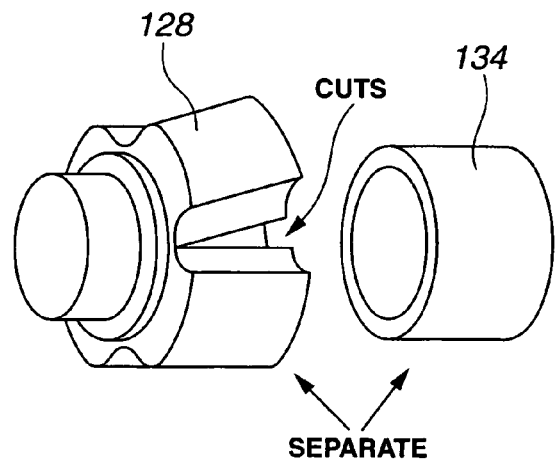
FIG. 14B is an explanatory diagram showing a situation wherein the fixing member and a CCD holding frame are separated in the state in FIG. 14A.
Figure 17:
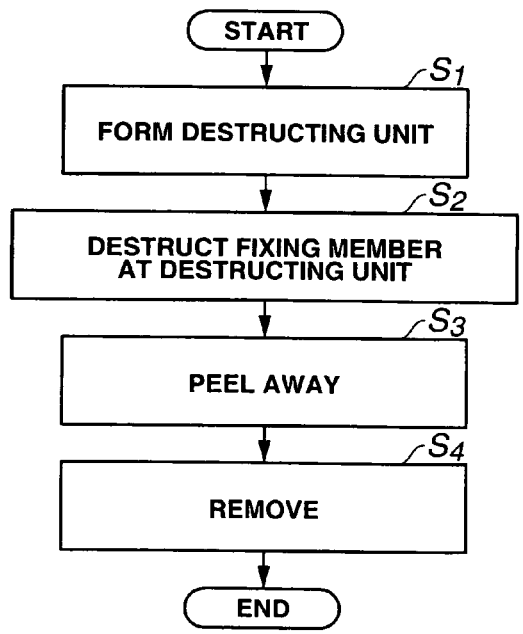
FIG. 17 is a flow chart for explaining a separating method.

FIG. 14A and FIG. 14B are explanatory diagrams illustrating an example of a disassembly method (separation method) in this case. FIG. 14A shows the fixing member 128 attached to the lens frame 122, and FIG. 14B shows the separation of the fixing member 128 and the CCD holding frame 134. FIG. 17 is a flow chart illustrating an example of a disassembly method.

As shown in FIG. 14A, the circumferential face of the fixing member 128 is processed to form a groove-shaped destructing portion 128-1 parallel to the objective lens axis (step S1 in FIG. 17). Note that the destructing portion 128-1 can be formed prior to assembly. One or more destructing portions 128-1 are formed on the circumferential face. Thus, cracking resistance of the destructing portion 128-1 is deteriorated with the attaching portion 128.

FIG. 14A shows an example wherein destructing portions 128-1 are formed in four location on the attaching portion 128, and by applying force in the diameter direction as to one block divided by the destructing portions 128-1, the block is destructed with the destructing portions 128-1 (step S2). Thus, the adhesive between the inner circumferential face of the fixing member 128 and the external circumferential face of the CCD holding frame 134 can be easily peeled off (step S3), and the fixing member 128 and the CCD holding frame 134 can be separated.

The CCD holding frame 134 and the lens frame 122 can be fitted together without adhesive with a fitting portion 139, and the CCD holding frame 134 and the lens frame 122 can be mutually removed without damaging the fitting portion 139 (step S4). In other words, the objective lens unit 121 and the image-capturing unit 130 can be separated.

Figure 15A:
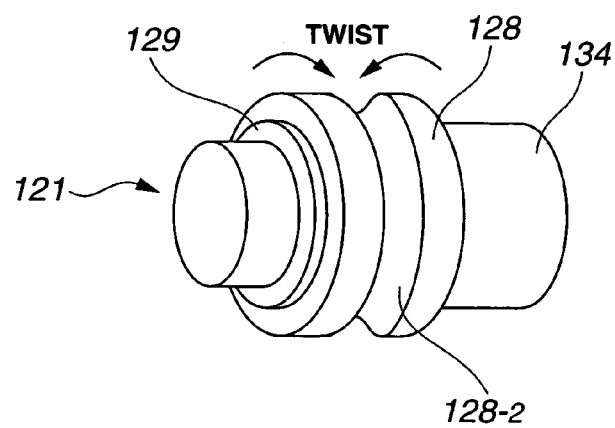
FIG. 15A is an explanatory diagram showing the fixing member of a configuration differing from that in FIG. 14A.
Figure 15B:
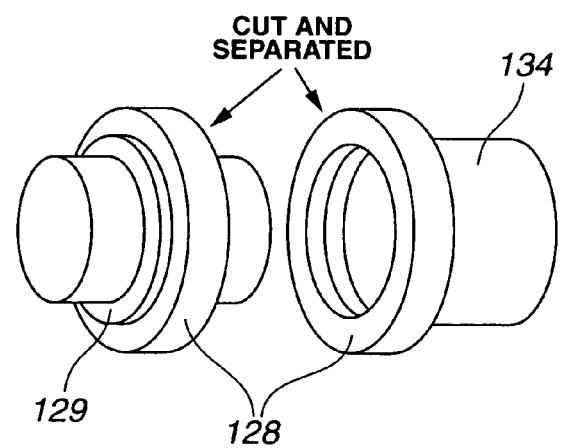
FIG. 15B an explanatory diagram showing a situation wherein the fixing member and a CCD holding frame are separated in the state in FIG. 15A.

Also, FIG. 15A and FIG. 15B are explanatory diagrams showing another example of a disassembly method. FIG. 15A shows the fixing member 128 attached to the lens frame 122, and FIG. 15B shows the separation of the fixing member 128 and the CCD holding frame 134.

As shown in FIG. 15A, the circumferential face of the fixing member 128 is processed to form a groove-shaped destructing portion 128-2 which is perpendicular to the axis of the objective lens. The destructing portion 128-2 is formed circumferentially on the circumferential face of the fixing member 128. Thus, cracking resistance of the destructing portion 128-2 is deteriorated with the attaching portion 128. In this case, the fixing member 128 is destructed with the destructing portion 128-2 by twisting the protruding portion 129 and the CCD holding frame 134 in mutually opposite directions.

Thus, the adhesive on the inner circumferential face of the fixing member 128 and the external circumferential face of the CCD holding frame 134 can be easily peeled off, and the fixing member 128 and the CCD holding frame 134 can be separated. In other words, the objective lens unit 121 and the image-captured unit 130 can be separated. For example, the destructing unit 128-2 is disposed in a location having the greatest clearance in the diameter direction of the lens frame 122 and fixing member 128. At this time, the destructing unit 128-2 is disposed in an appropriate position by the fixing member 128 abutting against the protruding portion 129.

With such a disassembly process, the fixing member 128 is configured with a material more flexible than that of the CCD holding frame 134, and therefore during the separation process, even if the fixing member 128 is damaged or broken, the CCD holding frame 134 almost never sustains damage. Also, even if the CCD holding frame 134 sustains damage during the separation process, this damage occurs only to the external circumferential face of the CCD holding frame 134, and does not occur to the fitting portion 139.

In this case, the CCD holding frame 134 and the lens frame 122 may be removed in a state wherein the lens frame 122 and the fixing member 128 remain joined together. Also, during removal, the adhesive in the adhesive portion 138 is also peeled off, and the lens frame 122 can become separated from the fixing member 128. Also, the fixing member 128 made of a flexible material can bend, and so the joining of the lens frame 122 and fixing member 128 can also separate. In either case, the fitting portion 139 of the CCD holding frame 134 and the lens frame 122 does not sustain any damage.

Thus, the image-capturing unit 130 held with the CCD holding frame 134 and the objective lens unit 121 held with the lens frame 122 are disassembled. In this separation process, at least the fitting portion 139 of the CCD holding frame 134 has not sustained any damage, and therefore, for example, in a case wherein only the objective lens unit 121 is replaced and the image-capturing unit 130 is to be reused, high precision axis-matching and focal point-matching can be performed.

Note that in the case of FIG. 15A, neither the objective lens unit 121 nor the image-capturing unit 130 have sustained damage, and so both of these can be reused.

Thus, with the present first modification, in the event of linking the lens frame and the CCD holding frame, the fitting portion which influences the objective lens axis and focal point matching is not adhered, and the lens frame and CCD holding frame are adhesively fixed with another portion. Therefore, in the case of disassembling the lens frame and the CCD holding frame, at least the fitting portion of the lens frame and CCD holding frame is prevented from sustaining damage, thus enable reusing after disassembly. For example, even in the case of a problem occurring such as debris or scratches in the objective lens unit, this can be disassembled and only the objective lens unit replaced, and by reusing the image-capturing unit, the image-capturing device can be reconfigured.

Figure 16:
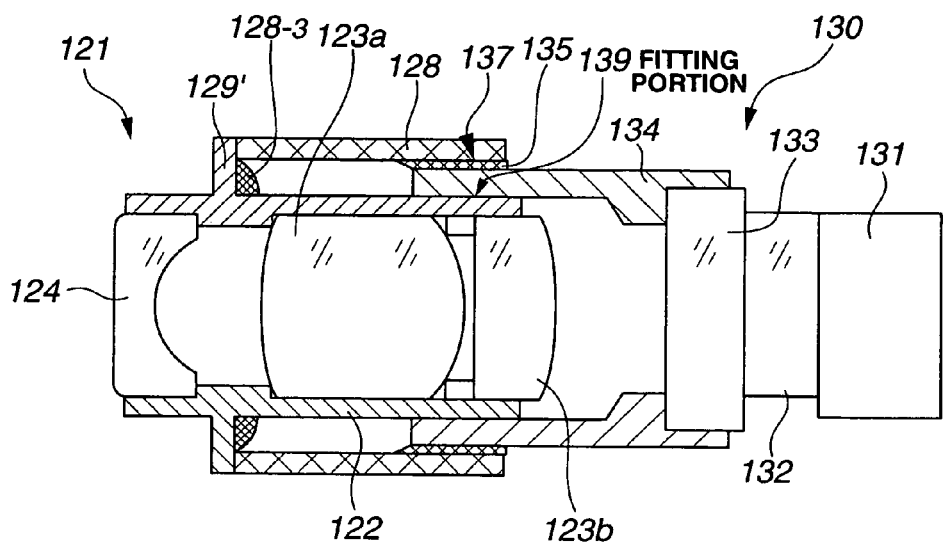
FIG. 16 is an explanatory diagram for explaining a separating method.

For example, as shown in FIG. 16, a configuration can be arranged such that the outer circumference of the CCD holding frame 134 and the inner circumference of the fixing member 128 are fit together, and the back face of the protruding portion 129' and the front end face of the fixing member 128 can be adhesively fixed with an adhesive 128-3. In this case, an unshown blade is inserted in the adhesive 128-3 so as to be perpendicular to the objective lens axis, and destructs by cutting. Alternatively, a solution can be used to swell or dissolve the adhesive 128-3. Thus, the objective lens unit 121 can be removed without sustaining any damage on the fitting portion of the protruding portion 129' and CCD holding frame 134. That is to say, in this case, the objective lens unit 121 can also be reused.

Thus, by changing the relation of the fitting between the fixing member, protruding portion and CCD holding frame, the reusable portions can also be changed.

Note that FIG. 11 describes an example wherein the lens frame 122 and fixing member 128 are configured with a separate unit, but the fixing member 128 and lens frame 122 can be configured integrally. In this case, the portion of the fixing member is also to be configured with the same material as with the lens frame.

Also, with the present first modification, an example is described wherein the lens frame is fitted to the inner circumference face of the CCD holding frame, but it goes without saying that an arrangement may be made wherein the CCD holding frame is fitted to the inner circumference face of the lens frame. In this case also, adhesive is not used on the fitting portion of the inner circumference face of the lens frame and the outer circumference face of the CCD holding frame, and the lens frame and the CCD holding frame can be adhesively fixed together at another portion.

Note that various configurations of the objective lens unit and image-capturing unit may be made as long as the configuration has each lens fixed to the lens frame, and the CCD and cover glass fixed or the like to the CCD holding frame, and it goes without saying the lens shape and numbers are not limited to those in FIG. 11, for example.

Also, according to the present first modification, the lens frame and image-capturing frame are fixed at a portion other than the fitting portion, and even if these parts are small, both frames can easily be fixed to one another, thus providing excellent workability. Also, a configuration is provided whereby the lens frame and image-capturing frame are fixed together via fixing member having a destructing portion, whereby the lens frame and image-capturing frame can be easily separated with a simple process of destructing the destructing portion. Also, even in the event that the image-capturing frame and lens frame are small, the two frames can be fixed together while maintaining workability with a relatively simple configuration. Also, the fixing member is fixed to the outer surface of the lens frame and the outer surface of the image-capturing frame, whereby attaching the fixing member is easier than the case of attaching the fixing member to the inner surface of the lens frame or image-capturing frame or both frames. Also, the destructing portion is formed with a material more flexible than the image-capturing frame, and so damage to the image-capturing frame can be effectively prevented in the event of destructing the destructing portion.

Note that a new fixing member may be used in the event of re-fixing the objective lens unit (lens frame) and image-capturing unit (image-capturing frame) after separation, and the fitting portion can be directly adhered to the lens without using a fixing member. The former case has the advantage wherein the parts can be reused in the case of performing repairs again, and the latter case has the advantage wherein the cost for parts is lowered because a fixing member is not used.

Figure 18:
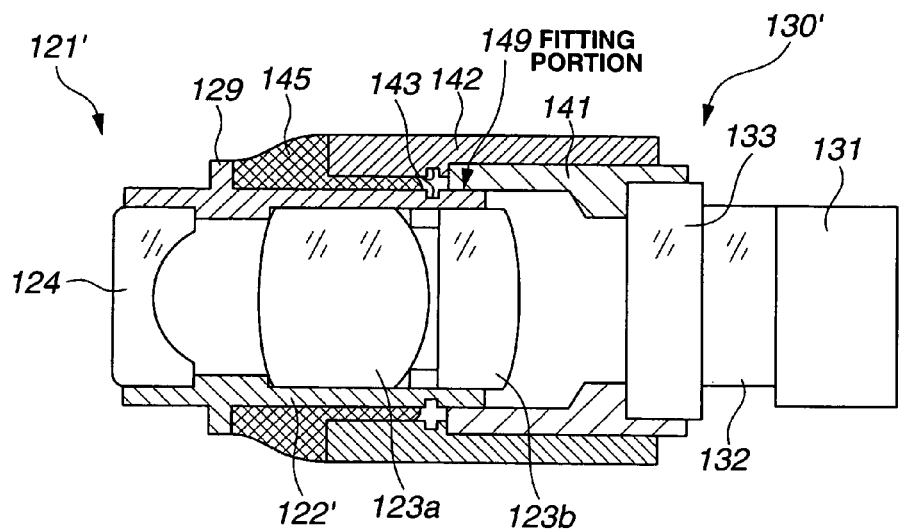
FIG. 18 is a cross-sectional view showing the image-capturing device according to a second modification.

FIG. 18 is a cross-sectional view of a second modification. In FIG. 18, the same reference numerals are used for the configuration elements which are the same as in FIG. 11, and description thereof will be omitted.

As described above, with a fitting portion influencing the objective lens axis and focal point matching, the lens frame and CCD holding frame are not adhered together, but by adhering the two frames together at another portion, the lens frame and CCD holding frame can be fixed to one another, and the shape and disposition of the fixing member and the like are not specifically restricted. The present second modification shows an example of attaching the fixing member to the CCD holding frame side.

In FIG. 18, the optical window member 124 and the lenses 123a and 123b which are fixed to the lens frame 122' are the same as those in FIG. 11, and the CCD 131, glass lid 132, and cover glass 133 configured integrally with the CCD holding frame 141 are also the same as those in FIG. 11. The lens frame 122' and the CCD holding frame 141 are respectively the same as the lens frame 122 or the CCD holding frame 134 regarding the inner diameter and outer diameter in FIG. 11. With the present second modification, the fixing member 142 equivalent to the fixing member 128 in FIG. 11 is adhesively fixed with an unshown adhesive on the outer circumferential surface of the CCD holding frame 141. Note that the fixing member 142 is configured with a material more flexible than the CCD holding frame 141, which is the same as with the first modification.

At the time of assembly, the lens frame 122' is fitted to the tip side inner circumferential face of the CCD holding frame 141. Thus, a high precision axis-matching can be performed. Note that both fitting portions 149 are not coated with adhesive.

The lens frame 122' is to be inserted in the fixing member 142. An adhesive 145 is filled in the space (adhesive portion) between the outer circumferential face of the lens frame 122' and the inner circumferential face of the fixing member 142, and upon performing focal point matching, the lens frame 122' and the fixing member 142 are mutually adhesively fixed.

A circumferential groove is formed on the outer circumferential face of the lens frame 122' nearer the tip side than the fitting portion 149 and on the inner circumferential face of the fixing member 142 on the tip side of the CCD holding frame 141, thus configuring an adhesive stopper 143 for preventing any adhesive 145 seeping out at the base side from reaching the fitting portion 149. By providing the adhesive stopper 143, an appropriate amount of adhesive 145 is disposed at the adhesive portion between the outer circumferential face of the lens frame 122' and the inner circumferential face of the fixing member 142, and also this completely prevents the adhesive 145 from reaching the fitting portion 149. Thus, an image-capturing device comprised with the objective lens unit 121' and the image-capturing unit 130' is obtained.

Here, the objective lens unit 121' and the CCD holding frame 141 are assumed to be disassembled for the purpose of repair or replacement. In this case, the adhesive 145 disposed in the portion wherein the outer circumferential face of the lens frame 122' and the inner circumferential face and the tip side face of the fixing member 142 are facing is peeled off. The fixing member 142 is configured with a material more flexible than that of the CCD holding frame 141, and therefore even if the fixing member 142 is damaged or broken during separation work, CCD holding frame 141 is rarely damaged. Also, even if the CCD holding frame 141 sustains damaged during the separation work, the damage thereof is limited to the outer circumferential face only of the CCD holding frame 141, and damage does not occur to the fitting portion 149.

Thus, with the present second modification also, in the event of disassembling the lens frame and the CCD holding frame, damage can be prevented from occurring to at least the fitting portion of the lens frame and CCD holding frame, thus enabling reuse after disassembly.

Figure 19:
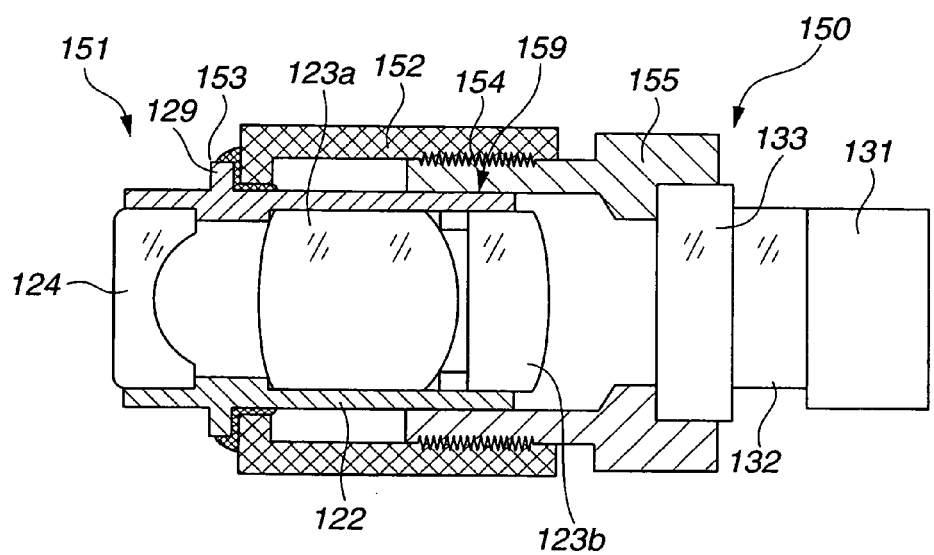
FIG. 19 is a cross-sectional view showing the image-capturing device according to a third modification.

Note that with FIG. 18, an example is described wherein the CCD holding frame 141 and the fixing member 142 are configured as separate units, but the fixing member 142 and the CCD holding frame 141 can be integrally configured. In this case, the fixing member portion is also configured with the same material as the CCD holding frame. FIG. 19 is a cross-sectional view of a third modification. In FIG. 19, the same reference numerals are used for the configuration elements which are the same as in FIG. 11, and the description thereof will be omitted.

In FIG. 19, the lens frame 122 and the optical window member 124 and the lenses 123a and 123b which are fixed to the lens frame 122 are the same as those in FIG. 11. With the present third modification, the integrally configured CCD 131, glass lid 132, and cover glass 133 are adhesively fixed to the CCD holding frame 155. The CCD holding frame 155 has the same inner diameter as the CCD holding frame 134, and the lens frame 122 can be fit into the fitting portion 159 serving as the tip side inner circumferential face.

With the present third modification, the fixing member 152 is configured in generally the same shape as the fixing member 128 in FIG. 11, and the inner diameter thereof generally matches the outer diameter of the tip side of the CCD holding frame 155. Also, on the outer circumferential face of the CCD holding frame 155 and the inner circumferential face of the fixing member 152, screw threads in the same screw shapes are mutually formed, and a screw portion 154 is configured. That is to say, using this screw portion 154, the CCD holding frame 155 can be screwed into the fixing member 152, thereby mutually fixing the CCD holding frame 155 and the fixing member 152.

In other words, at the time of assembly, the tip side inner circumferential face of the CCD holding frame 155 is fit into the lens frame 122, with the CCD holding frame 155 being screwed into the fixing member 152 and to be integrated. At the time of this fitting process, the objective lens axis matching and focal point matching are performed. Note that adhesive is not coated on the fitting portion 159 of the tip side inner circumferential face of the CCD holding frame 155 and the base side outer circumferential face of the lens frame 122.

The lens frame 122 is inserted from the tip side of the fixing member 152. In the state of having focal point matching performed, the adhesive 153 is filled in the space between the protruding portion 129 of the lens frame 122 and the tip face of the fixing member 152, and between the external circumferential face of the lens frame 122 and the inner circumferential face of the fixing member 152, thus mutually adhesively fixing the lens frame 122 and the fixing member 152. Thus, high precision axis matching and focal point matching between the objective lens unit 151 and the image-capturing unit 150 can be performed, and the image-capturing device is configured.

Here, the objective lens unit 151 and the CCD holding frame 155 are assumed to be disassembled for the purpose of repair or replacement. In this case, the adhesive 153 is peeled off, the objective lens unit 151 is rotated in the circumferential direction, and using the screw portion 154, the screwed joining between the fixing member 152 as well as the lens frame 122 and CCD holding frame 155 can be released. Thus, the objective lens unit 151 and the CCD holding frame 155 can be disassembled without causing any damage to the CCD holding frame 155 as well as the fitting portion 159.

Thus, with the present third modification also, similar advantages can be obtained as with the first and second modifications. Further, with the present third modification, there is the advantage of disassembly being much easier.

Note that with the present third modification, upon the fixing member 152 being adhesively fixed to the lens frame 122 beforehand, the screw portion 154 can be used to fit together the CCD holding frame 155 and the lens frame 122.

Figure 20:
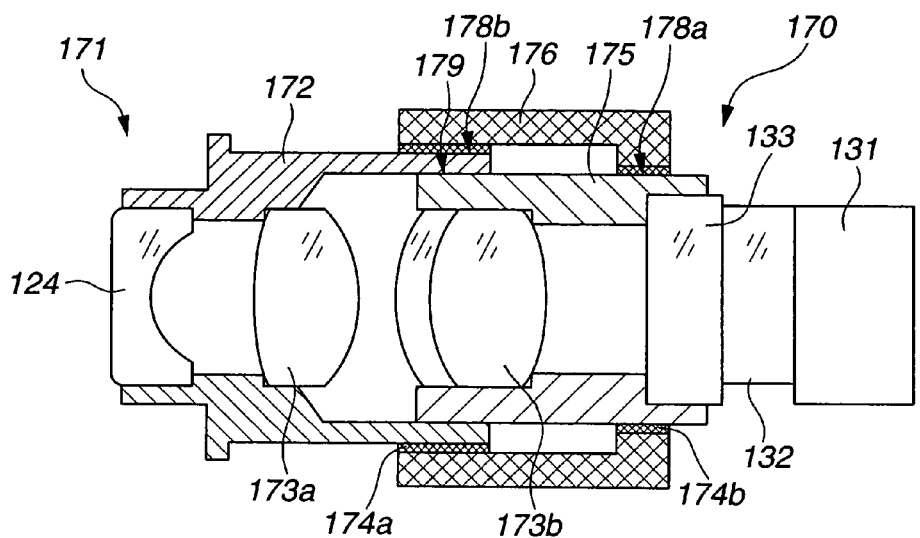
FIG. 20 is a cross-sectional view showing the image-capturing device according to a fourth modification.

FIG. 20 is a cross-sectional view showing a fourth modification. In FIG. 20, the same reference numerals are used for the configuration elements which are the same as in FIG. 11, and the description thereof will be omitted. The present fourth modification is an example applicable to an external fitting wherein the lens frame side is disposed on the outer side of the CCD holding frame.

In FIG. 20, the optical window member 124 and lenses 173a and 173b are adhesively fixed to a lens frame 172 configuring the objective lens unit 171 on the inner circumferential side thereof. On the other hand, the integrally configured CCD 131, glass lid 132, and cover glass 133 are adhesively fixed to a CCD holding frame 175, thus configuring an image-capturing unit 170.

With the present fourth modification, the outer diameter of the CCD holding frame 175 and the inner diameter of the lens frame 172 are generally the same, and the tip side of the CCD holding frame 175 is configured to fit into the base side inner circumferential face of the lens frame 172. Adhesive is not used on the fitting portion 179 between the tip side outer circumferential face of the CCD holding frame 175 and the base side inner circumferential face of the lens frame 172. By fitting together the CCD holding frame 175 and the lens frame 172 with the fitting portion 179, axis matching can be performed.

With the present fourth modification, a fixing member 176 is used on the outer side of the CCD holding frame 175 and lens frame 172, wherein the tip opening has an inner diameter slightly larger than the external diameter of the lens frame 172, and wherein the base side opening has an inner diameter slightly larger than the external diameter of the CCD holding frame 175.

At the time of assembly, the inner circumferential face of the fixing member 176 is adhered to the external circumferential face of one of the CCD holding frame 175 and lens frame 172. For example, the tip side of the CCD holding frame 175 is fit into the base side inner circumferential face of the lens frame 172, with the CCD holding frame 175 and fixing member 176 being in an adhesively fixed state by adhesive 178a. Then, upon performing axis matching and focal point matching, the outer circumferential face of the lens frame 172 and the inner circumferential face of the fixing member 176 are adhesively fixed with the adhesive 178b. Thus, high precision axis matching and focal point matching between the objective lens unit 171 and the image-capturing unit 170 can be performed, and the image-capturing device is configured.

Here, the objective lens unit 171 and the CCD holding frame 175 are assumed to be disassembled for the purpose of repair or replacement. In this case, for example, the adhesive 178a is peeled off, and the objective lens unit 171 is separated from the CCD holding frame 175. The adhesive is not used on the fitting portion 179, and so the objective lens unit 171 and the CCD holding frame 175 can be disassembled without causing any damage to the CCD holding frame 175.

Thus, with the present fourth modification also, similar advantages can be obtained as with the first through third modifications.

Figure 21:
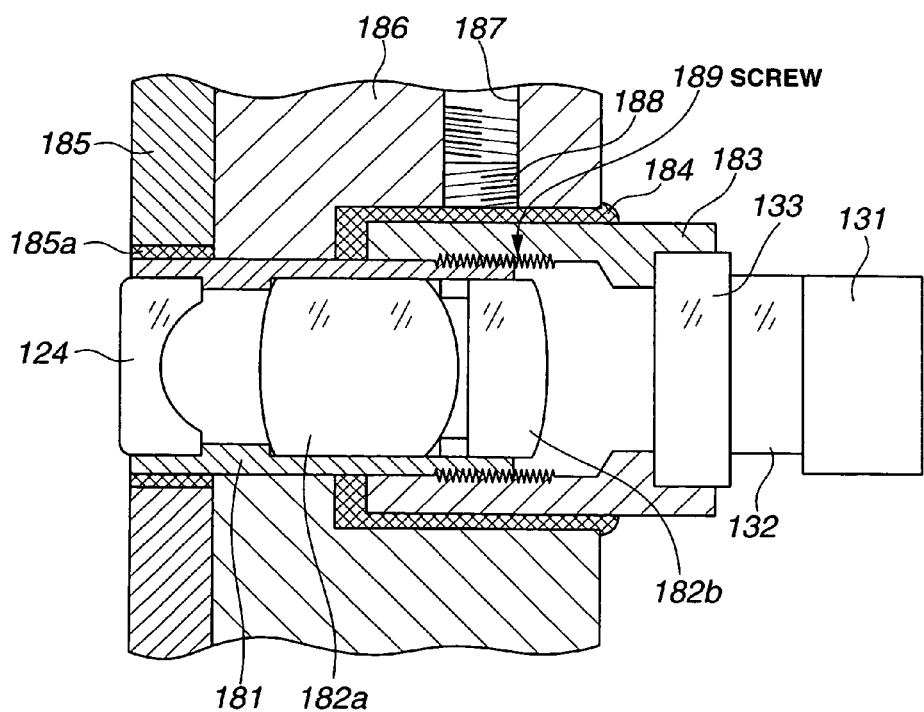
FIG. 21 is a cross-sectional view showing the image-capturing device according to a fifth modification.

Incidentally, in order to facilitate repair/disassembly, an arrangement may be considered wherein the lens frame and CCD holding frame are joined with a screw. FIG. 21 is a cross-sectional view of a configuration example in this case. In FIG. 21, the same reference numerals are used for the configuration elements which are the same as in FIG. 11, and the description thereof will be omitted.

In FIG. 21, the optical window member 124 and lenses 182a and 182b are adhesively fixed to a lens frame 181. On the other hand, the integrally configured CCD 131, glass lid 132 and cover glass 133 are adhesively fixed to a CCD holding frame 183. With the present fifth modification, the inner diameter of the CCD holding frame 183 and the outer diameter of the lens frame 181 is generally the same. Also, a screw portion 189 in the same screw shape is formed on the inner circumferential face of the CCD holding frame 183 and the outer circumferential face of the lens frame 181. Thus, the base side of the lens frame 181 can be screwed into the tip side inner circumferential face of the CCD holding frame 183. The fitting portion configured with the screw portion 189 does not have adhesive used thereupon. Axis matching can be performed with this fitting portion.

With the present fifth modification, a tip cover 185 is adhesively fixed to the outer circumferential face of the tip of the lens frame 181 by the adhesive 185a. As for the tip cover 185, a relatively flexible material such as plastic or acetal resin or the like, for example, is used. A tip rigid portion 186 is adhesively attached to this tip cover 185. Note that tip rigid portion 186 and the outer circumferential face of the lens frame 181 are not adhered. The tip rigid portion 186 is disposed between the CCD holding member 183 via an elastic adhesive 184.

With the present fifth modification, the tip rigid portion 186 has a screw hole 187 formed in the diameter direction in a position facing the CCD holding frame 183. By screwing a screw 188 into the screw hole 187, the CCD holding frame 183 can be fixed to the tip rigid portion 186. That is to say, the CCD holding frame 183 and the lens frame 181 are mutually fixed via the tip rigid portion 186 and the tip cover 185. Thus, after focal point matching the lens frame 181 is prevented from rotating as to the CCD holding frame 183, and so shifting of the focal point can be avoided.

Here, the lens frame and the CCD holding frame 183 are assumed to be disassembled for the purpose of repair or replacement. In this case, the adhesive 185a is peeled off, and the screw 188 is rotated so as to be removed from the screw hole 187. Then the lens frame 181 is rotated in the circumferential direction, and using the screw portion 189, the screwed joining of the lens frame 181 and CCD holding frame 183 is released. The fitting portion configured with the screw portion 189 enables disassembly of the lens frame 181 and the CCD holding frame 183 without causing any damage to the fitting portion.

Thus, with the present modification also, similar advantages can be obtained as with the first through fourth modifications.

Figure 22:
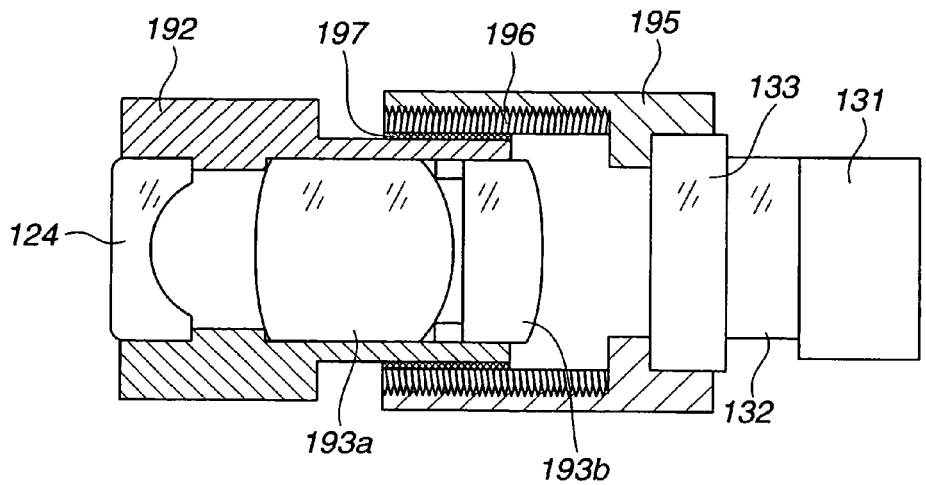
FIG. 22 is a cross-sectional view showing the image-capturing device according to a sixth modification.

Also, by configuring the fitting portion for the lens frame and CCD holding frame with a screw member, a configuration can be considered wherein the image-capturing unit can be reused, even in the case of using adhesive for the fitting portion. FIG. 22 is a cross-sectional view showing a configuration example in such a case. In FIG. 22, the same reference numerals are used for the configuration elements which are the same as in FIG. 11, and the description thereof will be omitted.

In FIG. 22, the optical window member 124 and lenses 193a and 193b are adhesively fixed to a lens frame 192. The integrally configured CCD 131, glass lid 132, and cover glass 133 are adhesively fixed to the CCD holding frame 195. With the present sixth modification, the CCD holding frame 195 has screw threads formed in the tip side inner circumference face thereof, and is configured so that a screw member 196 having a screw thread that matches this screw thread can be screwed into the inner circumferential face. The screw member 196 is cylindrically shaped, has a screw thread formed on the outer circumferential face thereof, and the inner circumferential face thereof is formed in a curved shape. The inner diameter of the screw member 196 is formed to be generally the same as the outer diameter of the lens frame 192.

The base side of the lens frame 192 is fitted into the inner circumferential face of the screw member 196 while in the state of the screw member 196 being screwed into the inner circumferential face of the CCD holding frame 195. Then the lens frame 192 and screw member 196 are adhesively fixed with an adhesive 197 at the fitting portion wherein the inner circumferential face of the screw member 196 and the outer circumferential face of the lens frame 192 are facing each other. At the time of this adhering, axis matching and focal point matching are performed. Here, the lens frame 192 and the CCD holding frame 195 are assumed to be disassembled for the purpose of repair or replacement. In this case, the adhesive 197 is peeled off, and the inner circumferential face of the screw member 196 and the outer circumferential face of the lens frame 192 are pulled apart, and the screw member 196 is pulled out of the lens frame 192. During this disassembly process, the inner surface of the screw member 196 sustains damage. However, the screw member 196 is screwed into the CCD holding frame 195, and so by removing the screw member 196 by rotating, the screw on the inner circumferential face of the CCD holding frame 195 is not damaged. Thus, by using a new screw member 196, the image-capturing unit other than the screw member 196 can be reused.

Thus, with the present sixth modification also, similar advantages can be obtained as with the first through fifth modifications.

Incidentally, in the case of linking the lens frame and the CCD holding frame, a rubber-type elastic adhesive wherein the adhesion force is relatively weak can be used as the adhesive, so as to minimize any damage from removing the adhesive from the fitting portion.

Figure 23:
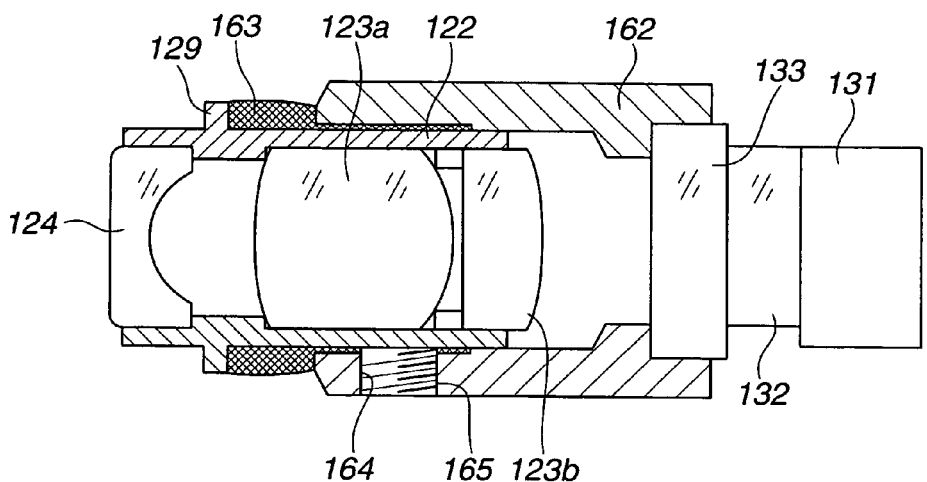
FIG. 23 is a cross-sectional view showing the image-capturing device according to a seventh modification.

FIG. 23 is a cross-sectional view showing such a configuration.

As shown in FIG. 23, the integrally configured CCD 131, glass lid 132 and cover glass 133 are adhesively fixed to the CCD holding frame 162. In FIG. 23, the joining face (fitting portion) of the CCD holding frame 162 and lens frame 122 has an elastic adhesive 163 such as a rubber type with weak adhesion coated thereon, and so the CCD holding frame 162 and lens frame 122 are mutually adhesively fixed. By using an elastic adhesive 163, a water-tight state can be secured.

Further, with the seventh modification in FIG. 23, the CCD holding frame 162 has a screw hole 164 provided in the diameter direction at a position facing the fitting portion with the lens frame 122, and upon completion of assembly, a screw 165 matching the screw shape of the screw hole 164 is screwed therein, and so the CCD holding frame 162 is tightened to the lens frame 122. Thus, the mutual fixing strength between the CCD holding frame 162 and lens frame 122 can be increased.

In the case of disassembling the lens frame 122 and CCD holding frame 162 for the purpose of repair or replacement, first, the screw 165 is removed, and then the adhesive 163 is peeled off. The adhesion force of the adhesive 163 is weak, so at the time of peeling off the adhesive 163, damage occurring to the fitting portion of the CCD holding frame 162 can be prevented.

Thus, in the example in FIG. 23 also, similar advantages can be obtained as with the first through sixth modifications.

Incidentally, the CCD configuring the image-capturing unit is connected to a cable with an electrical component configured with a TAB or the like. The vicinity of this electrical component needs to be covered with a metal so as to maintain strength, as well as secure clearance between the electrical component and the metal. However, as devices are made smaller, TABs are used more frequently, and so positioning the electrical component has been difficult.

Figure 24A:
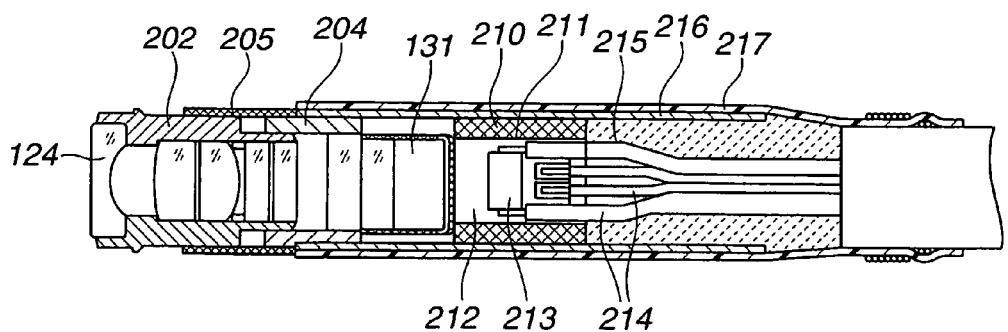
FIG. 24A is a cross-sectional view showing the image-capturing device according to an eighth modification.
Figure 24B:
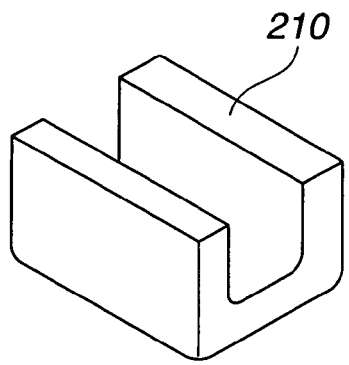
FIG. 24B is a perspective view of a holding member in FIG. 24A.

FIG. 24A and FIG. 24B show a solution for such problems occurring with the electrical components. FIG. 24A is a cross-sectional view showing the configuration of an endoscope tip portion, and FIG. 24B is a perspective view showing a holding member 210 in FIG. 24A.

A lens frame 202 is fitted into the tip side inner circumferential face of the CCD holding frame 204, and axis matching is performed. The CCD holding frame 204 and the lens frame 202 are mutually adhesively fixed by the fixing member 205 provided on the outer circumferential side thereof, and focal point matching is performed. The CCD 131 is fixedly attached to the base side of the CCD holding frame 204 via the cover glass.

An electronic component 211 configured with a TAB 212 or the like is disposed on the base side of the CCD 131. The electric component 211 is disposed with a small transistor or chip condenser or the like, or an electronic part 113 such as a chip resistor or an IC chip or the like. A composite cable 214 is connected to the electric component 211. The periphery of the CCD 131 and composite cable 214 is filled with adhesive 215, and on the further outer periphery thereof a metallic reinforcement frame 216 covers the outer circumference. Further, a heat-shrunk tube 217 is covering the outer circumference of this. The reinforcement frame 216 is adhesively fixed to the CCD holding frame 204.

With the eighth modifications shown in FIG. 24A, a holding member 210 formed of an insulating material is disposed so as to surround the electric component 211. The holding member 210 is in the form of a square with one side opened, having a bottom face and both sides as shown in FIG. 24B, with the electric component 211 being held in the portion surrounded by the bottom face and both sides. That distance between the inner faces of both side faces of the holding member 210 match the dimensions of the electric component 211, such that the electric component 211 does not move within the holding member 210.

Also, the outer faces of the both side faces of the holding member 210 are in contact with a reinforcement frame 216 whereby the holding member 210 functions as a positioning part for the electric component 211 along with the reinforcement frame 216. That is to say, the holding member 210 enables the clearance between the reinforcement frame 216 and the electric component 211 (TAB 212) to be minimized, so reduction in size can be enabled while maintaining sufficient strength.

Note that while an example of a direct-view image-capturing device has been illustrated in FIG. 24A, it is obvious that this arrangement can be similarly applied to the lateral-view image-capturing device shown in FIG. 4, wherein the image-capturing optical axis O generally orthogonal to the direction in which the electric component and cable extend.

Note that while the above modifications have been described with regard to an example wherein a CCD is used as the image-capturing device, the image-capturing device is not restricted in particular and this arrangement can be applied to all devices using a lens frame and an image-capturing frame for axis matching and focusing, and a CMOS sensor or the like may be used as the image-capturing device for example, which is obvious. According to the above-described configuration, pre-replacement parts can be reused at the time of repairing or replacing the image-capturing unit.

With the image-capturing device 26 shown in FIG. 4, a direct-view objective optical system 22 is employed, wherein the axis centers of all lenses generally match on a single axis, an arrangement which is basically widely employed in known direct-view type endoscopes.

Figure 7A:
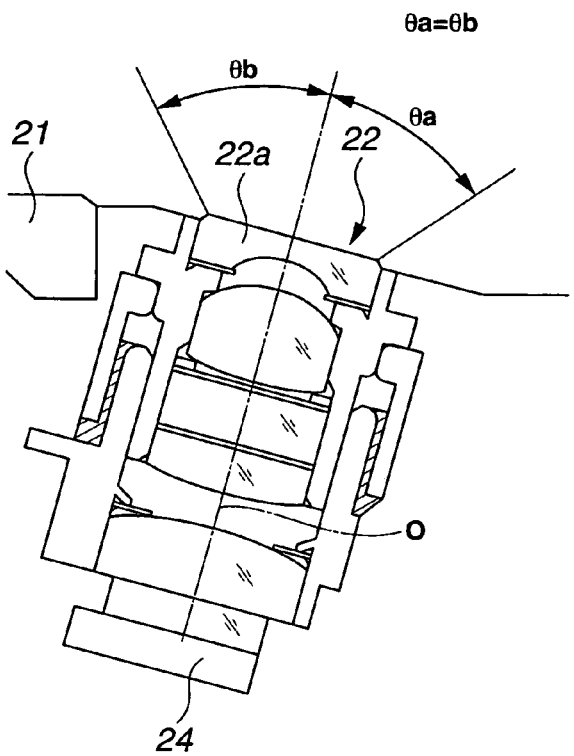
FIG. 7A is a diagram showing the configuration of an objective optical system portion wherein field of view angle setting means are formed with the image-capturing device.
Figure 7B:
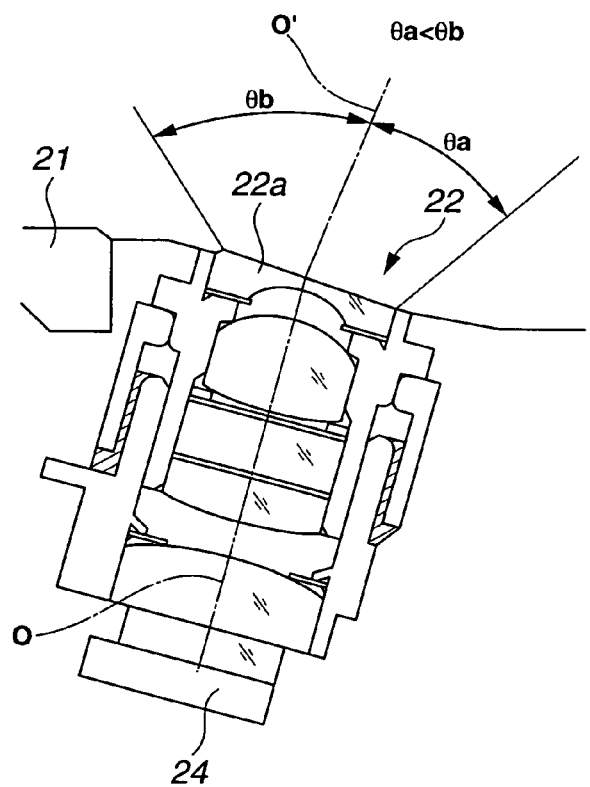
FIG. 7B is a diagram showing the configuration of an objective optical system portion wherein field of view angle setting means different from that in FIG. 7A is formed.

More specifically, the objective optical system 22 according to the present embodiment or the modifications thereof is an optical system such as shown in FIG. 7A or FIG. 7B.

In FIG. 7A, the axes of all lenses making up the objective optical system 22 (optical members) are situated in common along the image-capturing optical axis O which is illustrated as a single straight line, as with the case shown in FIG. 4, and further, in this case, field of view angle setting means are formed such that the upper field of view angle θa which is at the upper side of the image-capturing optical axis O of the objective optical system 22 or the direction of view (serving as a first field of view angle), and the lower field of view angle θb which is at the lower side (serving as a second field of view angle), are equal.

Note that in the embodiment, the path via which light rays inputted to the center of the image area of the CCD 24 pass through the objective optical system 22 to reach the center of the image area of the CCD 24 (in other words, an axis matching a line connecting the center of the image area of the CCD 24 and a path via which light rays inputted to the image area pass through the objective optical system 22) will be referred to as image-capturing optical axis (or simply optical axis) O to facilitate description.

FIG. 7A and FIG. 7B illustrate this by way of a cross-section taken along the axis of the objective optical system 22 and the center of the image-capturing face of the CCD 24 disposed at the image forming position of the objective optical system 22. This cross-section is parallel to the longitudinal direction of the tip portion 11 as shown in FIG. 2, and the image-capturing face of the CCD 24, which is a square for example, is bisected by this cross-section in a direction perpendicular to the plane of the drawings in FIG. 7A or FIG. 7B.

Also, with all of the lenses making up the objective optical system 22 shown in FIG. 7A, the axes of the lenses are each situated on a single image-capturing optical axis O, and all of the lenses are of rotationally symmetrical shapes. The field of view angle formed as a predetermined angle centered on the direction of view on the image-capturing axis O of the objective optical system 22 in FIG. 7A is also bisected by this cross-section in a direction perpendicular to the plane of the drawing in FIG. 7A.

Also, the field of view of the objective optical system 22 shown in FIG. 7A is bisected into a field of view having a range over a predetermined angle from the image-capturing optical axis O direction to the tip side of the insertion portion 7 with regard to this image-capturing optical axis O, i.e., the lower field of view angle θb, and a field of view having a range over a predetermined angle from the image-capturing optical axis O direction to the base side of the insertion portion 7, i.e., the upper field of view angle θa. That is to say, the upper field of view angle θa and the lower field of view angle θb are set so as to be equal, as shown in FIG. 7A.

Now, the upper field of view angle θa serving as the first field of view angle, and the lower field of view angle θb serving as the second field of view angle, correspond to the image-capturing regions Ia and Ib at the upper side and lower side of an image captured with the CCD 24, displayed on the monitor 6 as described below.

Figure 9A:
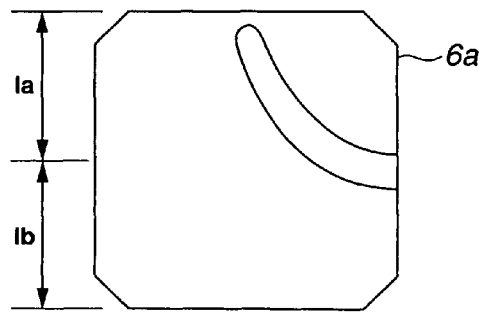
FIG. 9A is an explanatory diagram showing an endoscope image displayed on a monitor in the case of using the objective optical system in FIG. 7A.
Figure 9B:
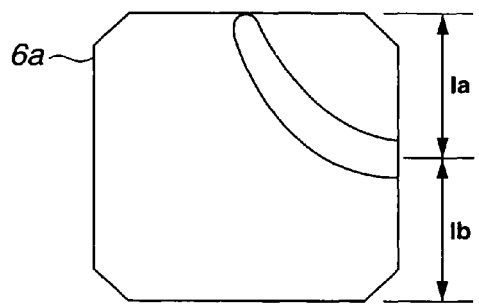
FIG. 9B is an explanatory diagram showing an endoscope image displayed on a monitor in the case of using the objective optical system in FIG. 7B.
Figure 9C:
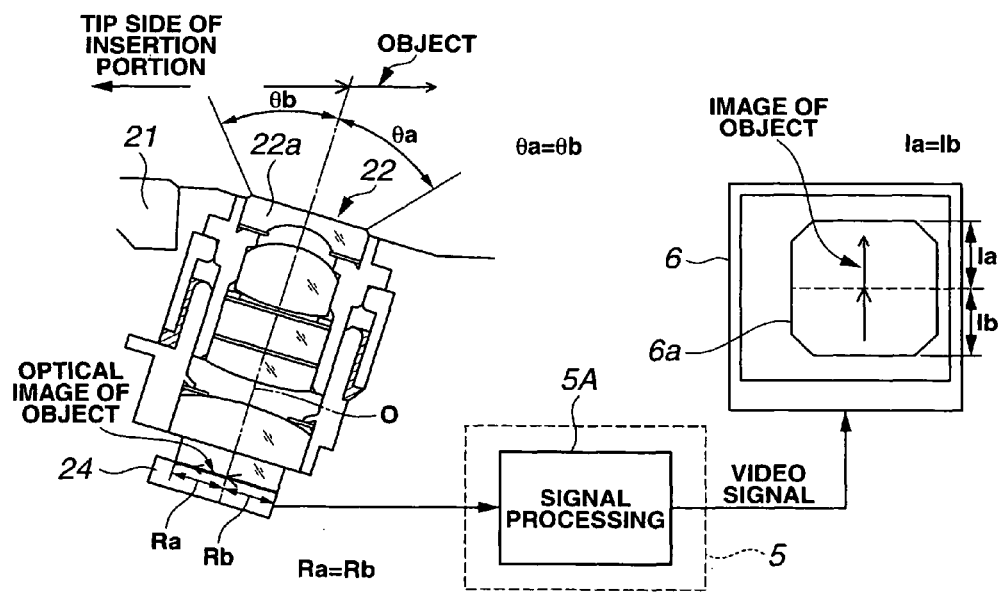
FIG. 9C is an explanatory diagram showing a situation of an image of an object being formed on a CCD and displayed on the monitor.

FIG. 9C illustrates the way in which an object indicated by an arrow is formed on the image-capturing face or photoreception face of the CCD 24 in the case of the image-capturing device shown in FIG. 7A, and the way in which the image of the object is subjected to signal processing in the signal processing circuit 5A within the video processor 5 and displayed in the endoscope image display area 6a of the monitor 6.

Note that the case shown in FIG. 7B differs from FIG. 7A where the conditions of θa=θb hold, whereas this is θa<θb in FIG. 7B.

The CCD 24 performs photoelectric conversion of the optical image of the formed object. The image-captured image subjected to photoelectric conversion by the CCD 24 is inputted to the signal processing circuit 5A, subjected to signal processing by the signal processing circuit 5A, and thus video signals are generated. The video signals are inputted to the monitor 6, and the monitor 6 displays the image of the subject corresponding to the video signals as an endoscope image. The user, such as a surgeon, can observe the image of the object displayed on the monitor 6.

With FIG. 9C, the sideways direction (horizontal direction) is parallel to the longitudinal direction of the insertion portion 7, and in this case, the left side is the tip side and the right side is the base side. As shown in FIG. 9C, the portion captured within the upper field of view angle θa of the subject is displayed on the display region Ia, which is the upper side of the endoscope image display area 6a of the monitor 6 from the vertically center portion thereof (meaning the same as saying the upper half display region). Also, the portion captured within the lower field of view angle θb of the subject is displayed on the display region Ib, which is the lower side of the endoscope image display area 6a of the monitor 6 (meaning the same as saying the lower half display region).

Also, in the case of the objective optical system 22 shown in FIG. 7A and FIG. 7B, the image captured with the upper field of view angle θa and the lower field of view angle θb is formed with an upper image-capturing region Ra for the tip side of the insertion portion 7 from the center of the CCD 24, and a lower image-capturing region Rb for the base side of the insertion portion 7. In the case of the objective optical system 22 shown in FIG. 7A and FIG. 7B, Ra=Rb and Ia=Ib hold, as shown in FIG. 9C.

In this case, in the case of the objective optical system 22 shown in FIG. 7A, θa=θb holds, so with both the optical image formed on the CCD 24, and the image displayed on the monitor 6, the upper side (upper half) and the lower side (lower half) are of the same magnification. Conversely, with the case of the objective optical system 22 shown in FIG. 7B, θa<θb holds, so with the optical image formed on the CCD 24 and the image displayed on the monitor 6, the upper side (upper half) has a magnification greater than that of the lower side (lower half).

Note that image-captured signals subjected to photoelectric conversion at the CCD 24 are inputted to the signal processing circuit 5A shown in FIG. 9C from the upper image-capturing region Ra side first for example, and the image-captured signals from the lower image-capturing region Rb later. The image-captured signals are then converted into video signals by the signal processing circuit 5A, and outputted to the monitor 6, starting from the image-captured image side captured with the upper image-capturing region Ra. The upper image-captured image is displayed on the upper side of the monitor 6.

In the case shown in FIG. 7A and FIG. 7B, the image-capturing face (photoreception face) of the CCD 24 is disposed perpendicular to the axis of the objective optical system 22, that is to say, the image-capturing face of the CCD 24 is disposed generally parallel to the longitudinal direction of the insertion portion 7. Thus, with the image-capturing device 26 according to the present embodiment, there is provided no refraction member for refraction of the incidence direction of light. That is to say, there is provided no refraction member such as a prism or mirror or the like for refraction of light within the lens group making up the objective optical system 22. In still other words, an observation image free of distortion occurring to a refraction member is provided, by disposing the objective optical system 22 and the CCD 24 such that the direction of field of view of the objective optical system 22 and the direction of the image-capturing face of the CCD 24 generally match (such that the axis of the objective optical system 22 is situated generally perpendicular to the image-capturing face of the CCD 24).

Also, as described above, the image-captured image formed on the left side (the tip side of the insertion portion 7) of the image-capturing face of the CCD 24 is displayed so as to be at the upper side when being displayed on the monitor 6 for observation, and image-captured image formed on the right side (the base side of the insertion portion 7) is displayed so as to be at the lower side when being displayed on the monitor 6 for observation.

Also, the image-capturing optical axis O is situated at the center of the image-capturing face (image area) of the CCD

24, with image captured at the field of view angles θa and θb being each formed at the left half and the right half from the center of the CCD 24.

In the case in FIG. 7A, the upper field of view angle θa forming the upper side image formed on the image-capturing face of the CCD 24, and the lower field of view angle θb forming the lower side image, are set so as to be equal. Conversely, with the case of the objective optical system 22 shown in FIG. 7B, the lower field of view angle θb is greater than the upper field of view angle θa, so with regard to the center of the image-capturing face, the upper side image-capturing region Ra and the lower side image-capturing region Rb are formed with different magnifications. Also, in the same way with the objective optical system shown in FIG. 7B, the image displayed on the monitor 6 is displayed at different magnifications for the upper side and lower side.

Thus, field of view angle setting means wherein, regarding the field of view angle centered on the field of view direction at the objective optical system 22, the first field of view angle taking the base side of the insertion portion 7 as the field of view range centered on the field of view direction, and the second field of view angle taking the tip side of the insertion portion as the field of view range, are set such that set to θa=θb in FIG. 7A.

The CCD 24 positioned at the image forming position of the objective optical system 22 has that which is captured at the upper field of view angle θa formed at the upper image-capturing region Ra (see FIG. 9C) toward the upper side at the time of observation which is at the tip side of the insertion portion 7, and that which is captured at the lower field of view angle θb formed at the lower image-capturing region Rb (see FIG. 9C) toward the lower side at the time of observation. In this case, image-capturing region setting means are formed such that the upper image-capturing region Ra and the lower image-capturing region Rb are equal.

In the case of the objective optical system 22 shown in FIG. 7A, the image captured by the CCD 24 is displayed on the endoscope image display area 6a of the monitor 6 as shown in FIG. 9A and FIG. 9C, as an endoscope image.

In FIG. 9A, the upper half (or upper side) image region corresponding to the field of view angle θa is denoted by reference symbol Ia, and the lower half (or lower side) image region corresponding to the field of view angle θb is denoted by reference symbol Ib. Note that FIG. 9A illustrates a schematic diagram showing a state of observing a treatment tool in the case of protruding the treatment tool in the state of the erecting block 32 at the maximum erecting angle, with the tip side of the treatment tool appearing (being displayed) at the upper side of the field of view range in most cases.

Setting the field of view angle such as shown in FIG. 7A allows the upper side and lower side of an image formed by the CCD 24 to be displayed in the endoscope image display area 6a of the monitor 6 at the same magnification. This is illustrated in FIG. 9C as θa=θb, Ra=Rb, Ia=Ib.

Accordingly, setting the field of view angle as shown in FIG. 7A or FIG. 9C solves the problem of the treatment tool being displayed small when observing due to widening the field of view at the upper side in the second preceding example, so an image which is larger and which is easier to observe is obtained.

Also, setting the field of view angle as shown in FIG. 7A is advantageous in that orientation of the treatment tool is easier due to the object displayed at the upper half of the observation image being displayed larger, as compared with the case of the preceding example wherein the field of view angle of the upper half is larger than the field of view angle of the lower half.

Also, the enlargement factor is generally the same at the upper half and lower half of the observation image, which is advantageous since an observation image which has little distortion in the vertical direction can be provided.

On the other hand, with the case of the modification shown in FIG. 7B, the axes of all lenses, excluding the first lens 22a serving as the optical component at the farthest tip of the components making up the objective optical system 22, are disposed along an axis represented as a single common line, and also the first lens 22a alone is formed of a wedge-shaped lens, wherein the farther toward the tip of the insertion portion 7 the thickener the lens thickness is, and the thickness is small toward the rear side. The direction of the image-capturing optical axis O is changed into an image-capturing optical axis O' by refraction toward the back of the insertion portion 7 by this first lens 22a. In the case of this modification, with regard to the incident side image-capturing optical axis O' of the objective optical system 22, the upper field of view angle θa is set so as to be smaller (narrower) than the lower field of view angle θb.

That is to say, with this arrangement, the portion with the narrow field of view angle θa is formed at the upper half of the image-capturing face of the CCD 24 (the upper image-capturing region Ra), and the portion with the wide field of view angle θb is formed at the lower half of the image-capturing face of the CCD 24 (the lower image-capturing region Rb), so the magnification of the image at the upper half is relatively greater than the magnification of the image at the lower half.

Accordingly, the image at the upper half can be displayed larger, and the image of the treatment tool displayed at the upper side can be displayed and observed larger.

In other words, the upper field of view angle θa corresponding to the image at the upper half that is formed on the image-capturing face of the CCD 24 is set so as to be narrower than the lower field of view angle θb corresponding to the image at the lower half. In this case, the image captured by the CCD 24 is displayed in the endoscope image display area 6a of the monitor 6 as an endoscope image, as shown in FIG. 9B.

In the case of FIG. 9B, the image of the treatment tool appearing within the upper field of view angle θa is displayed larger than with the case shown in FIG. 9A.

Setting the field of view angle such as shown in FIG. 7B displays the upper image-capturing region Ia corresponding to the upper field of view angle θa with an imaging magnification greater than the lower image-capturing region Ib corresponding to the lower field of view angle θb when displaying the image formed at the CCD 24, in the endoscope image display area 6a of the monitor 6.

Accordingly, the treatment tool and subject being observed as a small displayed image due to the upper field of view angle in the second preceding example can be solved, and observation can be made with a larger display and a state which is easier to observe.

In other words, setting the field of view angle as shown in FIG. 7B allows the image in the direction of protrusion of the treatment tool to be observed larger in comparison with the lower half, so the portion of interest at the time of treatment can be observed larger, while ensuring a field of view region equivalent to that of the proceeding example. Consequently, this is advantageous in that orientation of the treatment tool is further facilitated.

Thus, with the present embodiment and modifications thereof, when placing treatment tools or subjects in the field of view in particular to perform treatment, the display thereof is made larger, thereby further facilitating treatment. The CCD 24 is mounted on a TAB tape 27 shown in FIG. 25 at the inner side of the image-capturing frame 44 of the solid-state image-capturing unit 25. Note that FIG. 25 illustrates the front face (parts mounting face side) of the TAB tape 27, and FIG. 26 shows the reverse side thereof.

Note that pattern portions 27*b* and 27*d* are formed on the second layer on the upper face of the third-layer (polyimide) board resin 27*c* of the TAB tape 27 and the fourth layer thereof, with the upper face of the second-layer pattern portion 27*b* being covered with a first layer resist 27*a* and the base of the fourth-layer pattern portion 27*d* being covered with a fifth layer resist 27*e*.

Figure 25:
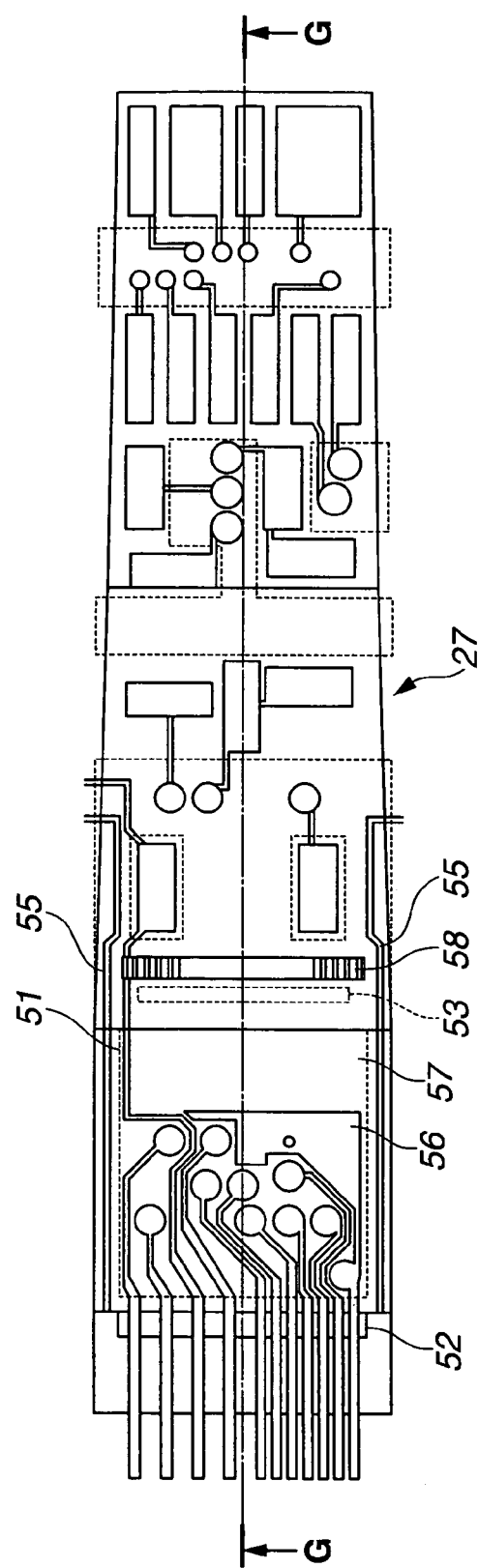
FIG. 25 is a plan view showing the configuration of a face (surface) of a part of a TAB tape.
Figure 26:
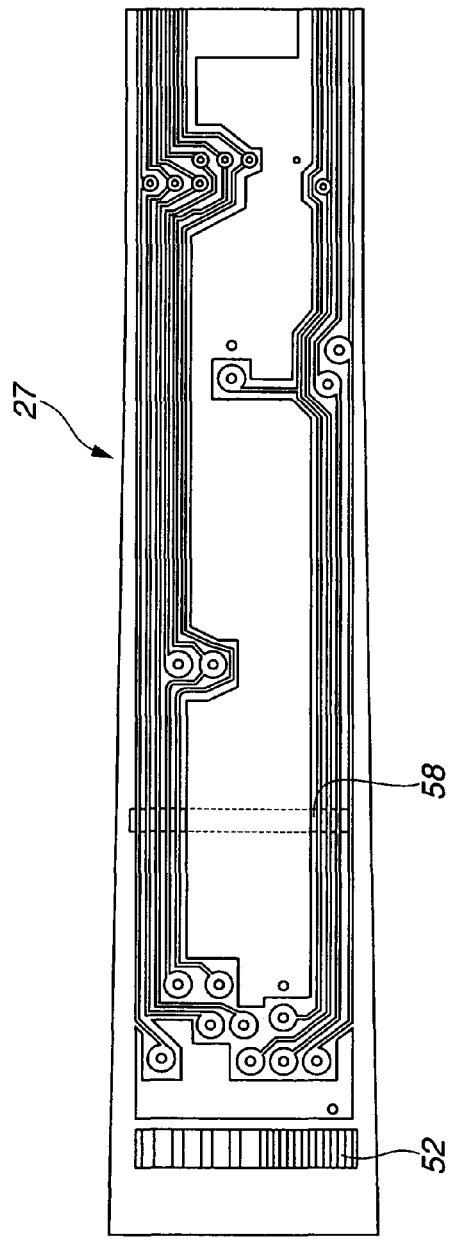
FIG. 26 is a plan view showing the configuration of the back face in FIG. 25.

With the present embodiment, a slit-shaped cut portion (pattern exposure portion) 52 is provided to the TAB tape 27 near the tip boundary of the region 51 indicated by the dotted line, where the CCD 24 is mounted as shown in FIG. 25, so as to leave both edges of the substrate resin, such that the TAB tape 27 can be easily bent at the cut portion 52. Note that the cut portion 52 is formed with the pattern portion being left and the cut portion 52 being exposed at the cut portion 52 (by removal of the polyimide board resin portion) (the same as with the later-described cut portion 58).

Figure 27A:
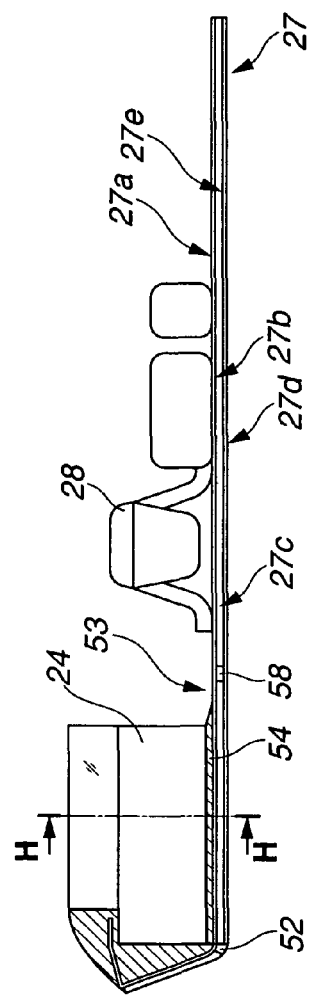
FIG. 27A is a cross-sectional view of the G-G line in a state wherein electronic parts and so forth are implemented to the TAB tape in FIG. 25.

Leads protruding from the tip of the TAB tape 27 are electrically connected to the CCD 24 as shown in FIG. 27A, and the tip side of the TAB tape 27 is bent at the cut portion 52 so as to be stored within the image-capturing frame 44 as shown in FIG. 4. Note that the tips of inner leads protruding from the TAB tape 27 are connected to bumps at the CCD 24.

Thus, providing a cut portion 52 at the tip side of the TAB tape 27 enables stable bending of the tip portion of the TAB tape 27. This bending allows the longitudinal-direction size of the image-capturing frame 44 to be reduced, and the length of the rigid portion of the tip portion main body 31 can be shortened.

Also, a recess 53 formed by removing (cutting) the first-layer resist of the TAB tape 27 is provided near the rear boundary of the region 51 where the CCD 24 is mounted to the TAB tape 27, as shown in FIG. 25. This recess 53 provides for a structure wherein overflow of adhesive agent 54 from the rear face of the CCD 24 to the TAB tape 27 side is suppressed with arrangements wherein the rear face of the CCD 24 is adhered to the TAB tape 27 with an adhesive agent 54, and also, the length of overflow can be visually recognized.

That is to say, in the event of adhesively fixing the rear face of the CCD 24 to the TAB tape 27 with an adhesive agent 54 in a state wherein the recess 53 is formed as shown in FIG. 25, this acts to stem overflow of the adhesive agent 54 to the back side at the boundary of the recess by surface tension, even in the event that the adhesive agent 54 does overflow from the rear face of the CCD 24 to the TAB tape 27 side as shown in FIG. 27A. Also, the general length of overflow can be (visually) grasped due to this recess 53 where the resist has been removed.

Moreover, damming dummy patterns 55 not electrically connected to the CCD are provided near both edges in the width direction of the region 51 where the CCD 24 is mounted, as shown in FIG. 25. Each of the dummy patterns 55 are formed protruding upwards slightly further than the inner portion where the dummy patterns 55 are not formed. The dummy patterns 55 protruding upwards serve to suppress overflowing of adhesive agent 54 in the width direction, in the event of fixing the rear face of the CCD 24 to the TAB tape 27 with adhesive agent 54.

Figure 27B:
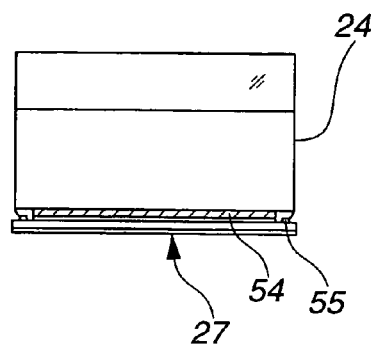
FIG. 27B is a cross-sectional view of the H-H line in FIG. 27A.

That is to say, as shown in FIG. 27B which is a cross-sectional view along line H-H in FIG. 27A, overflow of the adhesive agent 54 can be suppressed by the dummy pattern 55.

Note that the dummy patterns 55 extend further back than the CCD 24 as shown in FIG. 25, so as to not affect the surrounding patterns and the like.

Also, a ground pattern 56 is provided within the region 51 where the CCD 24 is mounted, as shown in FIG. 25, with the size of the ground pattern 56 being suppressed to only one portion toward the center for example, thereby forming a region 57 for pooling adhesive agent 54 at the portion where the ground pattern 56 is not provided.

Thus, forming a region 57 for pooling the adhesive agent 54 enables the amount of overflow to the surroundings to be reduced or suppressed.

Also, a cut portion 58 where the polyimide resin portion has been cut (removed) in a slit shape is provided near the back boundary of the region 51 where the CCD 24 is mounted to the TAB tape 27, adjacent to the above recess 53 to be specific, as shown in FIG. 25 and FIG. 26, with the bending strength being reduced at the cut portion 58 so as to be easily bendable. Note that the polyimide resin portion has been removed at this cut portion 58, thereby forming a pattern exposure portion where the wiring pattern is exposed. Also note that an arrangement may be made wherein the thickness of the polyimide resin is made thinner so as to reduce the bending strength thereof, thereby obtaining a structure which is easily bent.

That is to say, the TAB tape 27 with the CCD 24 and so forth mounted thereto, in a state of being slightly bent at the cut portion 58 and with an adhesive agent 59 or a filler being filled therein as shown in FIG. 4, is fixed within the image-capturing frame 44. Further, adhesive agent 59 is filled in above the flange of the second lens frame 42 (protruding from the back side in the longitudinal direction) as well. The tilting endurance of the image-capturing device 26 (tilting the solid-state image-capturing unit 25 as to the objective optical system unit 23) is improved by the strength (when hardened) of the adhesive agent 59.

In this case, further backward from the cut portion 58 of the TAB tape 27 is positioned and fixed within the image-capturing frame 44 and shield frame 45 so as to be parallel with the longitudinal direction of the tip portion 11. The TAB tape 27 is bent until being parallel with the longitudinal direction of the tip portion 11 at the least, so as to reduce the height of the image-capturing device 26 (distance in the lateral-view direction).

Also, electronic parts 28 such as transistors and the like are mounted on the TAB tape 27 with a slight distance from the position where the bending cut portion 53 has been provided adjacent to the position where the CCD 24 is fixed by adhesion, as shown in FIG. 27A.

Thus, even in the event that adhesive agent 54 overflows to the TAB tape 27 side, the electric parts 28 are mounted with a slight distance therebetween, so the TAB tape 27 can be bent at a position desirable for bending.

Also, as shown in FIG. 25, the TAB tape 27 is formed tapered such that the width at the back end is smaller than the side at the tip (front end).

Accordingly, at the time of the CCD 24 being mounted to the tip side of the TAB tape 27, even in cases of the longitudinal direction of the TAB tape 27 inclining somewhat, the CCD 24 can be stored within a predetermined width better than compared with an untapered shape, since the width of the back end side is reduced in a tapered shape.

Also, at portions other than the position where the TAB tape 27 is to be bent, electronic parts 28 are provided as shown in FIG. 27A so as to be unbending. Thus, the TAB tape 27 can be made rigid due to mounting of the electronic parts 28 at positions other than where bending thereof is desired, thereby realizing stable handling.

Figure 28:
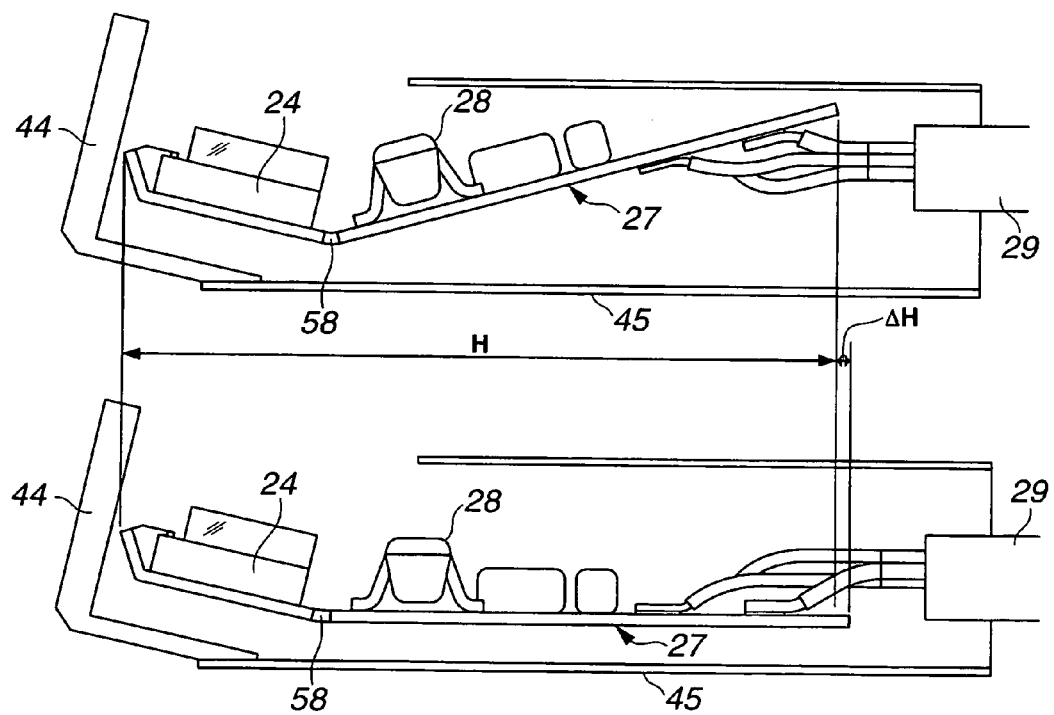
FIG. 28 is a diagram showing a portion of the image-capturing device according to a modification.

With the above description, a great portion of the TAB tape 27 is extended in the horizontal direction of the tip portion 11 at the cut portion 58 formed to the TAB tape 27, but an arrangement may be made wherein the length H in the horizontal direction of the TAB tape 27 is made shorter than that shown in FIG. 4 by bending further, as shown in FIG. 28 (the upper part of the drawing).

Note that FIG. 28 is a schematic diagram illustrating around the TAB tape 27 according to FIG. 4 to the bottom for comparison, showing that the horizontal length can be reduced by ΔH as compared with this case.

Accordingly, the length can be made shorter than that of the shield frame 45, and the rigid length at the tip portion can be further shortened.

Note that as shown at the upper part of FIG. 28, the signal lines of the signal cable 29 should be connected to the rear face of the TAB tape 27 in order to facilitate storage within the shield frame 45.

With the lateral-view type electronic endoscope image-capturing device according to the preceding example, the TAB tape of the solid-state image-capturing device is laid out in the longitudinal direction of the insertion portion, so that the length of the TAB tape affects the length of the image-capturing rigid portion and the rigid portion length is long, as shown in FIG. 28 the length in the longitudinal direction of the insertion portion 7 is reduced by bending the TAB tape 27 at the cut portion 58, thereby achieving the object of reducing the rigid length of the image-capturing device 26.

Also, with the present embodiment, as with the case of using a treatment tool in the second preceding example for example, the tip side of the treatment tool at the time of maximally erecting the erecting block 32 is captured within the upper field of view angle θ, thereby ensuring compatibility such that approximately identical treatment operations can be performed. With the second preceding example, the upper field of view angle is set wider than the lower field of view angle, so in the event of erecting the erecting block maximally, the tip side of the treatment tool when protruding from the tip portion by around 20 mm can be captured within the widened upper field of view angle.

Also, the user will often restrict the amount of protrusion of the treatment tool beforehand such that the tip end portion of the treatment tool does not go outside from the upper field of view angle, to perform treatment.

Conversely, with the present embodiment, the first lens 22a in the objective optical system 22, which is a lens differing from that in the second preceding example, is used. As described above, the upper field of view angle θa is made smaller (more narrow) than the lower field of view angle θb, as compared with the case of the second preceding example.

Due to the upper field of view angle θa having been made smaller, in the event that the user uses the treatment tool in the same configuration of other parts with the second preceding example, there is the possibility that the tipmost portion of the treatment tool may go outside from the visible range (the upper field of view angle θa) at the time of protruding the treatment tool from the tip opening 19a of the treatment tool channel 19 and erecting the erecting block 32 maximally.

Figure 29:
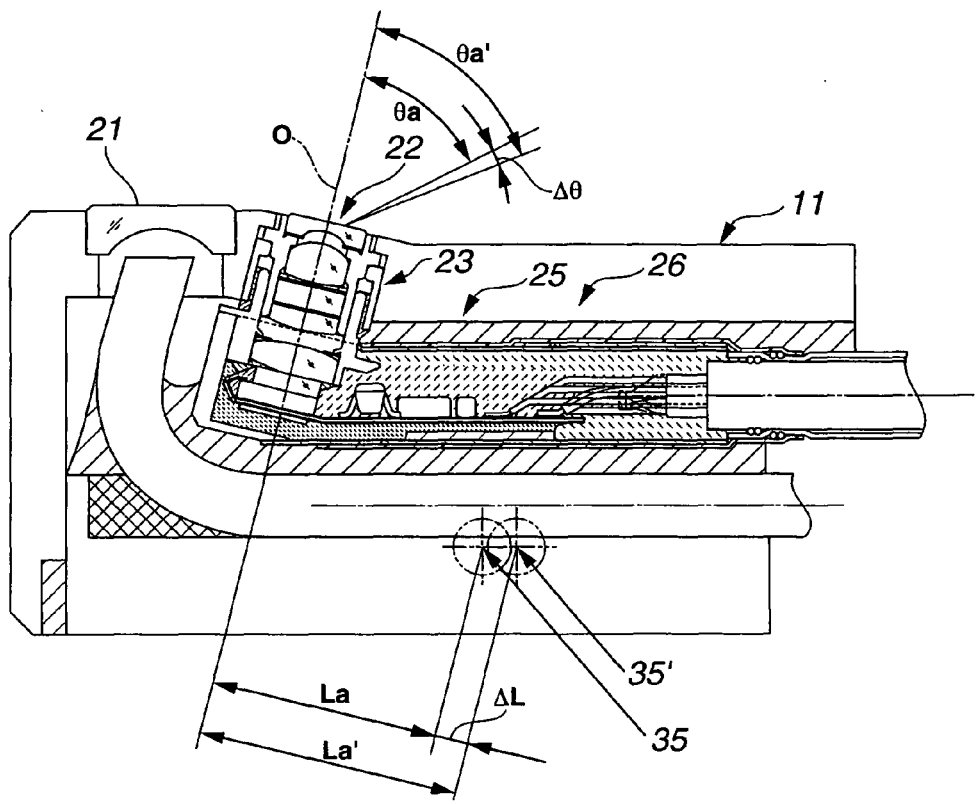
FIG. 29 is an explanatory diagram of the configuration having compatibility so as to capture the tip side of the treatment tool in the field of vision, similar to a case of a known electronic endoscope.

Accordingly, with the present embodiment, the position of the erecting base shaft 35 of the erecting block 32 is shifted toward the tip from that in the second preceding example, as shown in FIG. 29. That is to say, a configuration is made wherein the erecting block 32 is turnably (rotatably) supported on the erecting block shaft 35 at a position shifted toward the tip side at the tip portion main body 31.

More specifically, with the upper field of view angle according to the present embodiment as θa, the upper field of view angle in the preceding example as θa', and also the distance between the image-capturing optical axis O and the erecting block shaft 35 as La and the distance between the image-capturing optical axis O and the erecting block shaft 35' as La', the value of difference in distance La'–La (difference distance ΔL=La'–La) is increased by the degree in which the upper field of view angle θa' is greater than the field of view angle θa, i.e., by the difference Δθ (=θa'–θa) of θa'–θa, and in this case, set such that Δθ/θa'≤ΔL/La'.

Thus, the distances La' and La between the shafts 35' and 35 rotatably supporting the image-capturing optical axis O and erecting block 32 between the preceding example and the present embodiment are increased or reduced by an amount corresponding to the difference in the upper field of view angles θa' and θa. In other words, with the present embodiment, the position of the rotating block shaft 35 is shifted toward the tip side of the insertion portion 7 by a predetermined amount, as opposed to the position of the rotating block shaft 35' for rotatably supporting (serving as a rotational shaft for) the erecting block, where the widened upper field of view angle θa' is formed in the preceding example. By shifting this predetermined amount, the position of the tip of the treatment tool appearing at the upper field of view angle θa side is shifted downwards (downwards parallel movement) overall as compared to a case with no shifting, and set such that the tipmost portion thereof does not go outside from the upper side of the upper field of view angle θa.

According to such a configuration, the field of view range (field of view angle) wherein image-capturing can be performed by the CCD 24 and the position of the erecting block are set so as to enable ensuring of compatibility with the preceding example (with regard to the function of keeping the tip portion of the treatment tool within the field of view range) such that treatment can be performed with the tip inside the field of view range, in the event of using the treatment tool with the present embodiment.

Figure 30:
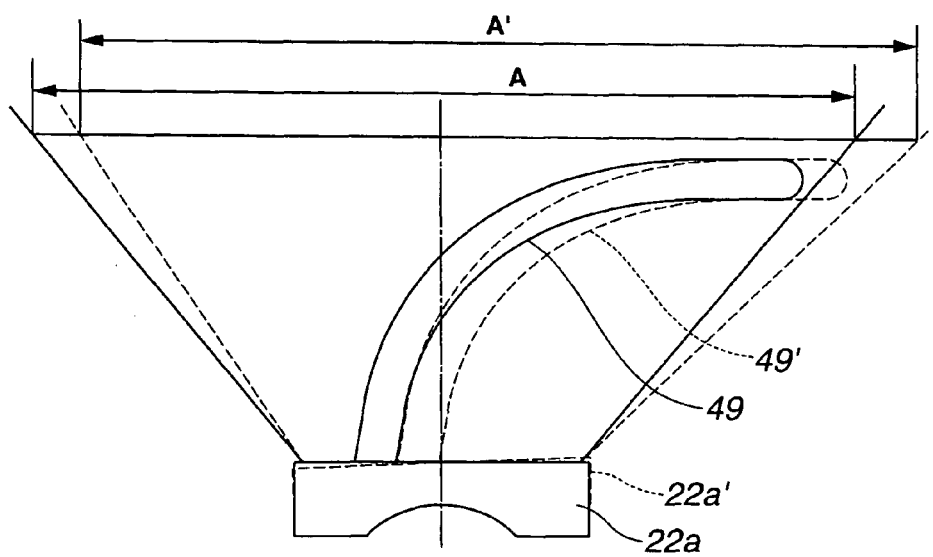
FIG. 30 is an explanatory diagram of the action of FIG. 29.

The operations in this case will be shown in FIG. 30.

In FIG. 30, the first lens 22a' and the field of view range A' shown with dotted lines indicate the case of the preceding example, and in comparison the first lens 22a and the field of view range A shown with solid lines indicate the case of the present embedment. As shown in FIG. 30, according to the present embodiment as to the preceding example, the field of view range in the vertical direction shifts toward the tip side (the lower field of view angle side) from A' to A due to the change in the field of view angle by the first lens 22a (FIG. 30 is a simplified view showing the horizontal direction range).

Accordingly, with the preceding example the tip of the treatment tool 49' indicated by dotted lines stays within the field of view range A', but a part of the tip of the treatment tool 49' would not fit within the field of view angle as it is due to shifting of the field of view range toward the tip side as indicated by A with the present embodiment, however, the direction in which the treatment tool is protruded is changed so as to be protruded from a position shifted toward the tip side at the base side from which the treatment tool is protruded, as described with FIG. 29.

That is to say, in the event of protruding the treatment tool 49 shown with solid lines by around 20 mm, the tip thereof can be kept within the field of view range A, by making the curve which the treatment tool follows as indicated by dotted lines to have guide properties shifted to the tip side of the insertion portion 7.

Thus, in the case of performing treatment by protruding the tip side of the treatment tool with the erecting block 32 erected to the maximum angle, the tip side of the treatment tool protruding can be captured in the field of view range with the present embodiment as with the preceding example, so excellent operability can be ensured. Also, with a case of configuring an endoscope system having the electronic endoscope of the preceding example and the electronic endoscope 2 according to the present embodiment, compatibility can be ensured regarding the function of capturing the tip side of the treatment tool within the field of view range by erecting operations of the erecting block 32.

The operations according to the present embodiment with such a configuration will be described. A case of endoscope examination of around the duodenum for example, using the electronic endoscope 2, will be described.

In the event of observing the duodenum, a lateral-view endoscope which enables observation toward the side of the insertion direction of the endoscope is suitable. The insertion portion 7 of the electronic endoscope 2 according to the present embodiment is inserted, and in addition to observing the duodenal papilla, the treatment tool may be guided to the bile duct or pancreatic duct thereat for treatment.

In such a case, the treatment tool is inserted from the treatment tool insertion opening 19b so that the tip side of the treatment tool protrudes from the tip opening 19a.

Also, operating the erecting operation knob 38 to realize the maximum erecting angle allows the image of the tip portion of the treatment tool protruded to the image region Ia side at the generally upper half within the image displayed in the endoscope image display area 6a as shown in FIG. 9A.

In this case, the tip portion of the treatment tool and the subject can be displayed larger than with the preceding example as described above, thereby facilitating introduction of the treatment tool to the bile duct or pancreatic duct, and also facilitating treatment with the treatment tool, thereby enabling improving operability with the treatment tool to be improved.

Also, with the present embodiment, the tip portion of the erected treatment tool can be kept within the observation field of view range by providing the erecting block shaft 35 which rotatably supports the erecting block 32 further toward the tip side than with the preceding example, also enabling operability of using the treatment tool.

Second Embodiment

Figure 31:
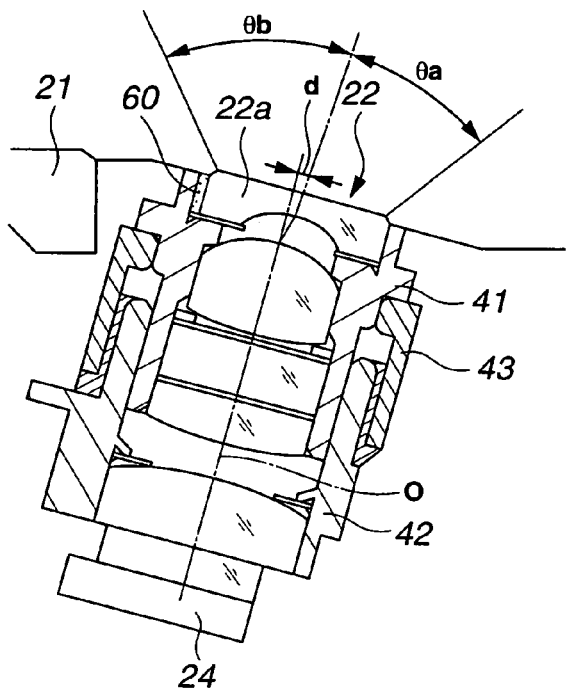
FIG. 31 is a cross-sectional view showing a partial configuration of an image-capturing device according to a second embodiment of the present invention.

Next, a second embodiment of the present invention will be described with reference to FIG. 31. FIG. 31 illustrates the configuration of the objective optical system portion of the image-capturing device according to the second embodiment of the present invention. With this embodiment, the first lens 22a in the objective optical system 22 according to the first embodiment for example, is shifted in a direction orthogonal to the axis of the lens system other than the first lens 22a, such that the upper field of view angle θa is smaller than the lower field of view angle θb.

That is to say, as shown in FIG. 31, the axis of the first lens 22a is moved in a direction orthogonal to the image-capturing optical axis O, the direction being away from the upper field of view angle side (back side of the insertion portion 7 in the longitudinal direction), i.e., away from the illumination lens 21 of the tip portion 11 (by a movement distance of d, for example), and is fixed to the lens frame 41 with an adhesive agent 60. The movement distance d is, in other words, the offset amount as to the axis of the objective optical system 22, as to the center of the image area of the image-capturing device.

In this case, while the shape of the hole on the upper end of the first lens frame 41 in the first embodiment was a circular shape to fit to the outer diameter of the first lens 22a, with the case of the present embodiment the shape is changed from a circle to an oblong hole of an elongated circle, with the first lens 22a being deviated backwards and fixed by an adhesive agent 60.

Due to the first lens 22a being shifted backwards and fixed to the first lens frame 41, the gap at the front side of the first lens 22a first lens frame 41 is filled with the adhesive agent 60 and is fixed, as shown in FIG. 31.

With such a configuration, in a case of making the upper field of view angle θa to be smaller than the lower field of view angle θb in approximately the same way as with the first embodiment using a simple configuration, and using the treatment tool, the treatment tool can be observed in a large manner.

Description will be made regarding the fact that in this case, in the event of moving the axis of the first lens 22a to the tip side orthogonally to the image-capturing optical axis, i.e., to the lower field of view angle θb side, and attaching, the upper field of view angle θa becomes smaller, with reference to FIG. 32A and FIG. 32B. Note that in the following description, the field of view angle θa will be represented by α, and the field of view angle θb will be represented by β.

Figure 32A:
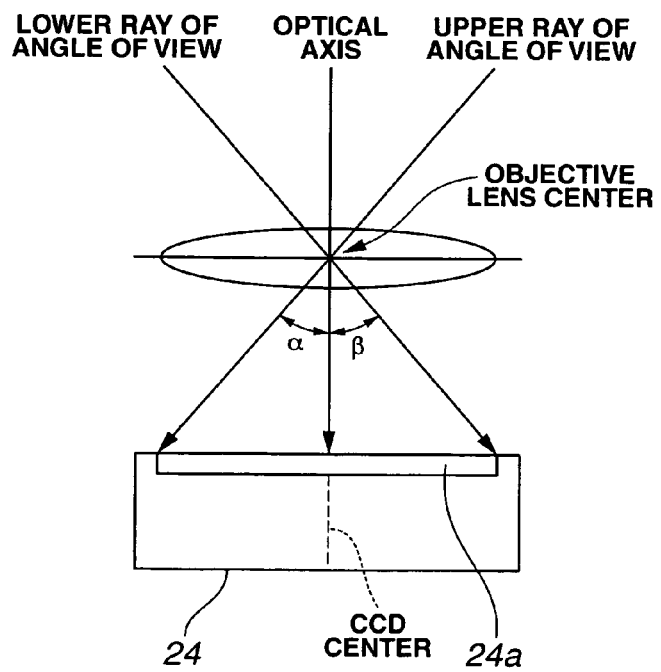
FIG. 32A is an action explanatory diagram in the case wherein a first lens is not moved with the configuration in FIG. 31.

FIG. 32A illustrates a state wherein the axis of the first lens 22a is not moved and is situated on the axis of the objective optical system. Note that in FIG. 32A and FIG. 32B, the objective optical system 22 is illustrated as being a single objective lens.

In this case, incident rays following the axis of the objective lens which follow the image-capturing optical axis, are received at the center position of the photoreception face 4a of the CCD 24.

Also, as shown in FIG. 32A, incident rays to the objective optical system (objective lens) which follow the upper field of view angle α (called upper field of view angle rays), and incident rays to the objective optical system which follow the lower field of view angle β (lower field of view angle rays), are received at the respective edges of the photoreception face 24a.

In this state, the relation in magnitude between the field of view angles α and β is

α=β.

Figure 32B:
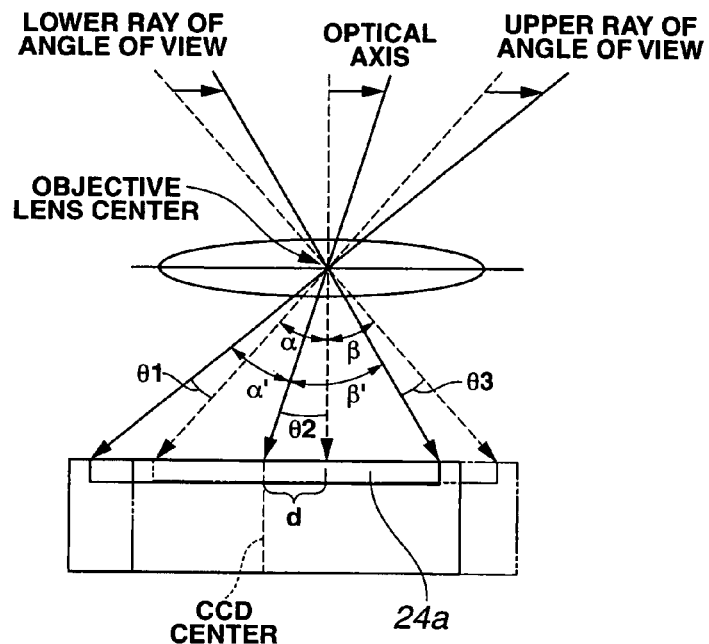
FIG. 32B is an action explanatory diagram in the case of the configuration in FIG. 31.

In the event of moving the first lens 22a toward the lower field of view angle side by a relative distance d as with the second embodiment, this is equivalent to moving the image-capturing optical axis toward the upper field of view angle side as shown in FIG. 32B. Note that in FIG. 32B, the dotted lines indicate the state in FIG. 32A. In the state in FIG. 32B, the following hold:

Upper field of view angle α'=α+θ1−θ2

Lower field of view angle β'=β+θ2−θ3

Now, the relation in magnitude between θ1, θ2, and θ3 is, from the geometric relation shown in FIG. 32B,

θ2>θ3>θ1 and accordingly the relation in magnitude between α' and β' is, based on

α'<α,β<β',

α'<β'.

At this time, the regions of the photoreception face 24a where the rays of α' and β' are inputted are equal.

Due to the above relation, the upper field of view angle α' and the lower field of view angle β' have the same region on the photoreception face 24a, whereby the upper field of view angle α' is made smaller than the lower field of view angle β' such that the magnification of the upper field of view angle α' in the endoscope image can be made greater than the magnification of the lower field of view angle β'. According to the present embodiment, advantages approximately the same as those of the first embodiment can be obtained.

Figure 33A:
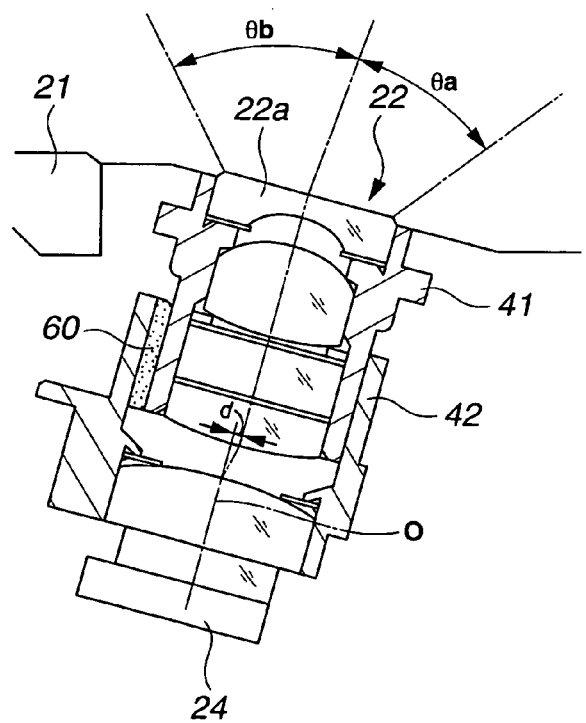
FIG. 33A is a cross-sectional view showing a partial configuration of an image-capturing device according to a first modification.

While the present embodiment has a configuration wherein the first lens 22a of the objective optical system 22 according to the first embodiment has been moved, an arrangement may be made as a first modification, wherein instead of moving the first lens 22a, the first lens frame 41 is moved backwards as to the second lens frame 42, as shown in FIG. 33A.

Accordingly, the second lens frame 42 has been described as a shape fitting with the back end of the first lens frame 41 in the first embodiment, but here is formed with an oblong cross-sectional shape for example, fixed with the adhesive agent 60 in a state of the first lens 22a being shifted backwards (the direction away from the illumination lens 21) from the axis of the lenses to the back thereof.

The first lens frame 41 side is shifted backwards and fixed to the second lens frame 42, so a shown in FIG. 33A, the gap formed at the front side of the first lens frame 41 and second lens frame 42 is filled with adhesive agent 60 and fixed.

Figure 33B:
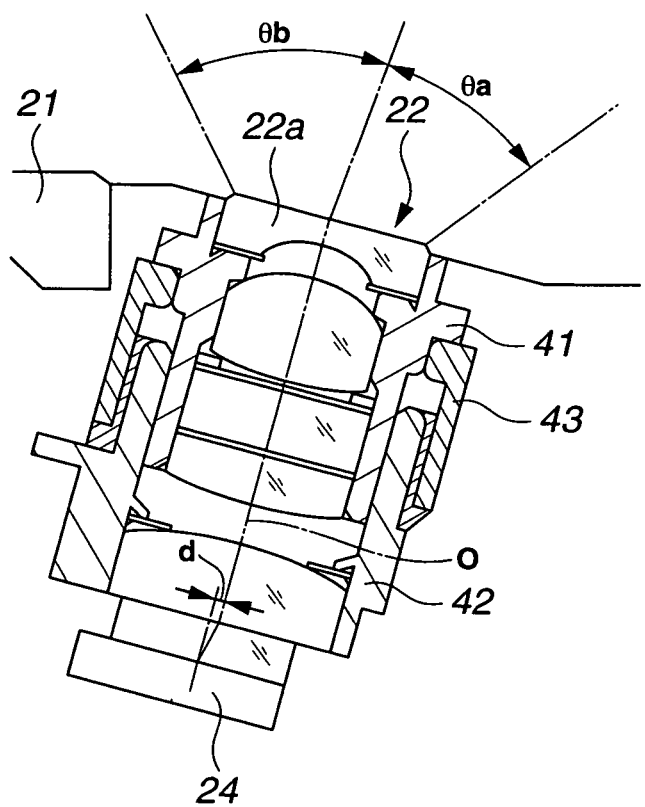
FIG. 33B is a cross-sectional view showing a partial configuration of an image-capturing device according to a second modification.

This first modification has advantages similar to those of the present embodiment. Additionally, the CCD chip 24 side may be moved forward from the axis of the objective optical system 22, as with a second modification shown in FIG. 33B.

In the above-described embodiments, image distortion may be corrected by a video signal processing circuit within the video processor 5 in the event of forming the size of the upper and lower field of view angles to be different.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An image-capturing apparatus comprising:
   a lens frame having a shape of a cylinder in which one or more lenses are fixed;
   an image-capturing frame having a shape of a cylinder in which an image-capturing device is fixed, the image-capturing frame being arranged such that an inner circumferential surface of the image-capturing frame is in direct contact with an outer circumference surface of the lens frame over an entire periphery of the image-capturing frame, or an outer circumferential surface of the image-capturing frame is in direct contact with an inner circumferential surface of the lens frame over an entire periphery of the image-capturing frame; and
   a fixing member for fixing the lens frame and the image-capturing frame to each other without adhesion between a part of the lens frame and a part of the image-capturing frame which are in direct contact with each other,
   wherein the inner circumferential surface or the outer circumference surface of the lens frame has a contact part in contact with the image-capturing frame and a non-contact part out of contact with the image-capturing frame, and the fixing member connects the lens frame and the image-capturing frame at a position other than a vicinity of a boundary between the contact part and the non-contact part.

2. An image-capturing apparatus comprising:
   a lens frame having a shape of a cylinder in which one or more lenses are fixed;
   an image-capturing frame having a shape of a cylinder in which an image-capturing device is fixed, the image-capturing frame being arranged such that an inner circumferential surface of the image-capturing frame is in direct contact with an outer circumference surface of the lens frame over an entire periphery of the image-capturing frame, or an outer circumferential surface of the image-capturing frame is in direct contact with an inner circumferential surface of the lens frame over an entire periphery of the image-capturing frame; and
   a fixing member for fixing the lens frame and the image-capturing frame to each other at a portion other than a part of the lens frame and a part of the image-capturing frame which are in direct contact with each other,
   wherein the inner circumferential surface or the outer circumference surface of the lens frame has a contact part in contact with the image-capturing frame and a non-contact part out of contact with the image-capturing frame, and the fixing member connects the lens frame and the image-capturing frame at a position other than a vicinity of a boundary between the contact part and the non-contact part.

3. The image-capturing apparatus according to claim 1, wherein the fixing member has a destructing portion which is destructed when separating the lens frame and the image-capturing frame.

4. The image-capturing apparatus according to claim 2, wherein the fixing member has a destructing portion which is destructed when separating the lens frame and the image-capturing frame.

5. The image-capturing apparatus according to claim 1, wherein the fixing member is fixed to an outer surface of the lens frame and an outer surface of the image-capturing frame.

6. The image-capturing apparatus according to claim 2, wherein the fixing member is fixed to an outer surface of the lens frame and an outer surface of the image-capturing frame.

7. The image-capturing apparatus according to claim 1, wherein the destructing portion of the fixing member is configured with a material more flexible than that of the image-capturing frame.

8. The image-capturing apparatus according to claim 2, wherein the destructing portion of the fixing member is configured with a material more flexible than that of the image-capturing frame.

9. A fixing device for an image-capturing apparatus comprising:
   a fixing member for holding and fixing to each other a lens frame having a shape of a cylinder in which one or more lenses are fixed and an image-capturing frame having a shape of a cylinder in which an image-capturing device is fixed, the image-capturing frame being arranged such that an inner circumferential surface of the image-capturing frame is in direct contact with an outer circumference surface of the lens frame over an entire periphery of the image-capturing frame, or an outer circumferential surface of the image-capturing frame is in direct contact with an inner circumferential surface of the lens frame over an entire periphery of the image-capturing frame, such that an image-capturing face of the image-capturing device is positioned at a focus position of the one or more lenses,
   wherein the fixing member holds and fixes the lens frame and the image-capturing frame at a portion other than a part of the lens frame and a part of the image-capturing frame which are in direct contact with each other, and wherein the inner circumferential surface or the outer circumference surface of the lens frame has a contact part in contact with the image-capturing frame and a non-contact part out of contact with the image-capturing frame, and the fixing member connects the lens frame and the image-capturing frame at a position other than a vicinity of a boundary between the contact part and the non-contact part.

10. The fixing device for an image-capturing apparatus according to claim 9, wherein the fixing member holds and fixes to each other the lens frame and the image-capturing frame at a portion other than the contact surfaces between the lens frame and the image-capturing frame.

11. The fixing device for an image-capturing apparatus according to claim 9, wherein the fixing member has a destructing portion which is destructed when separating the lens frame and the image-capturing frame.

12. The fixing device for an image-capturing apparatus according to claim 10, wherein the fixing member has a destructing portion which is destructed when separating the lens frame and the image-capturing frame.

13. The fixing device for an image-capturing apparatus according to claim 9, wherein the fixing member is fixed to an outer surface of the lens frame and an outer surface of the image-capturing frame.

14. The fixing device for an image-capturing apparatus according to claim 10, wherein the fixing member is fixed to an outer surface of the lens frame and an outer surface of the image-capturing frame.

15. The fixing device for an image-capturing apparatus according to claim 11, wherein the fixing member is fixed to an outer surface of the lens frame and an outer surface of the image-capturing frame.

16. The fixing device for an image-capturing apparatus according to claim 11, wherein the destructing portion of the fixing member is configured with a material more flexible than that of the image-capturing frame.

17. A repair method for an image-capturing apparatus comprising steps of:
destructing a fixing member for fixing a lens frame having a shape of a cylinder in which one or more cylindrical lenses are fixed and an image-capturing frame having a shape of a cylinder in which an image-capturing device is fixed to each other, the image-capturing frame being arranged such that an inner circumferential surface of the image-capturing frame is in direct contact with an outer circumference surface of the lens frame over an entire periphery of the image-capturing frame, or an outer circumferential surface of the image-capturing frame is in direct contact with an inner circumferential surface of the lens frame over an entire periphery of the image-capturing frame, the fixing member connecting the lens frame and the image-capturing frame at a position other than a vicinity of a boundary between a contact part in which the inner circumferential surface or the outer circumference surface of the lens frame is in contact with the image-capturing frame and a non-contact part in which the inner circumferential surface or the outer circumference surface of the lens frame is out of contact with the image-capturing frame, and releasing fixing between the frames;
replacing at least either of the lens frame and the image-capturing frame; and
fixing the lens frame and the image-capturing frame using a new fixing member configured to hold and fix the lens frame and the image-capturing frame at a portion other than a part of the lens frame and a part of the image-capturing frame in direct contact with each other.

18. The repair method for image-capturing apparatus according to claim 17, wherein either the lens frame or the image-capturing frame is replaced in the replacing step, and the replaced one of the lens frame and the image-capturing frame is fixed to the other one of the lens frame and the image-capturing frame in the fixing step.

* * * * *